(12) United States Patent
Ryazanov et al.

(10) Patent No.: US 8,030,286 B2
(45) Date of Patent: Oct. 4, 2011

(54) METHODS AND MEANS FOR INCREASING RESISTANCE TO CELL DAMAGE

(75) Inventors: Alexey G. Ryazanov, Princeton, NJ (US); Hsueh-Ping Chu, Taipei (TW)

(73) Assignee: University of Medicine and Dentistry of New Jersey, Somerset, NJ (US)

( * ) Notice: Subject to any disclaimer, the term of this patent is extended or adjusted under 35 U.S.C. 154(b) by 661 days.

(21) Appl. No.: 11/615,690

(22) Filed: Dec. 22, 2006

(65) Prior Publication Data

US 2008/0119429 A1 May 22, 2008

Related U.S. Application Data

(63) Continuation-in-part of application No. PCT/US2005/022741, filed on Jun. 24, 2005.

(60) Provisional application No. 60/819,688, filed on Jul. 10, 2006, provisional application No. 60/582,411, filed on Jun. 24, 2004.

(51) Int. Cl.
*A61K 48/00* (2006.01)
*A61K 31/00* (2006.01)

(52) U.S. Cl. .......................................... 514/44 A; 514/1
(58) Field of Classification Search ............. 514/1, 44 A
See application file for complete search history.

(56) References Cited

U.S. PATENT DOCUMENTS

| 6,624,170 B2 * | 9/2003 | Giovanella et al. ........... 514/283 |
| 2002/0142429 A1 * | 10/2002 | Ryazanov et al. ............ 435/194 |

* cited by examiner

*Primary Examiner* — J. E. Angell
(74) *Attorney, Agent, or Firm* — Fox Rothschild LLP

(57) ABSTRACT

Methods are provided to increase resistance to cell damage in a subject. The increase in resistance to cell damage in a subject in the subject is accomplished by decreasing activity of eEF2 kinase in the subject. The eEF2 kinase activity can be decreased by decreasing the amount of functional eEF2 kinase produced by the subject, including contacting the eEF2 kinase with a compound that inhibits phosphorylation of eEF2 kinase substrate or decreasing the amount of functional eEF2 kinase is decreased by reducing expression of a gene encoding the eEF2 kinase.

7 Claims, 7 Drawing Sheets

SEQUENCE LISTING

```
<160> NUMBER OF SEQ ID NOS: 4

<210> SEQ ID NO 1
<211> LENGTH: 2178
<212> TYPE: DNA
<213> ORGANISM: Homo sapiens

<400> SEQUENCE: 1
atggcagacg aagacctcat cttccgcctg gaaggtgttg atggcggcca gtcccccccga       60 gctggccatg atggtgattc tgatggggac agcgacgatg aggaaggtta cttcatctgc      120
cccatcacgg atgacccaag ctcgaaccag aatgtcaatt ccaaggttaa taagtactac      180
agcaacctaa caaaaagtga gcggtatagc tccagcgggt ccccggcaaa ctccttccac      240
ttcaaggaag cctggaagca cgcaatccag aaggccaagc acatgcccga ccctgggct       300 gagttccacc tggaagatat tgccaccgaa cgtgctactc gacacaggta caacgccgtc      360
accggggaat ggctggatga tgaagttctg atcaagatgg catctcagcc cttcggccga      420
ggagcaatga gggagtgctt ccggacgaag aagctctcca acttcttgca tgcccagcag      480
```

```
tggaagggcg cctccaacta cgtggcgaag cgctacatcg agcccgtaga ccgggatgtg      540
tactttgagg acgtgcgtct acagatggag gccaagctct ggggggagga gtataatcgg      600
cacaagcccc ccaagcaggt ggacatcatg cagatgtgca tcatcgagct gaaggacaga      660
ccgggcaagc ccctcttcca cctggagcac tacatcgagg gcaagtacat caagtacaac      720
tccaactctg gctttgtccg tgatgacaac atccgactga cgccgcaggc cttcagccac      780
ttcactttgg agcgttccgg ccatcagctg atagtggtgg acatccaggg agttggggat      840
ctctacactg acccacagat ccacacggag acgggcactg actttggaga cggcaaccta      900
ggtgtccgcg ggatggcgct cttcttctac tctcatgcct gcaaccggat tgcgagagc      960 atgggccttg ctccctttga cctctcgccc cgggagaggg atgcagtgaa tcagaacacc     1020
aagctgctgc aatcagccaa gaccatcttg agaggaacag aggaaaaatg tgggagcccc     1080
cgagtaagga ccctctctgg gagccggcca cccctgctcc gtcccctttc agagaactct     1140
ggagacgaga acatgagcga cgtgaccttc gactctctcc cttcttcccc atcttcggcc     1200
acaccacaca gccagaagct agaccacctc cattggccag tgttcagtga cctcgataac     1260
atggcatcca gagaccatga tcatctagac aaccaccggg agtctgagaa tagtggggac     1320
agcggatacc ccagtgagaa gcggggtgag ctggatgacc ctgagccccg agaacatggc     1380
cactcataca gtaatcggaa gtacgagtct gacaagacag cctgggcag ctctggacgg     1440 gtatgtgtag agaagtggaa tctcctcaac tcctcccgcc tccacctgcc gagggcttcg     1500
gccgtggccc tggaagtgca aaggcttaat gctctggacc tcgaaaagaa aatcgggaag     1560 tccatttttgg ggaaggtcca tctggccatg gtgcgctacc acgagggtgg gcgcttctgc     1620
gagaagggcg aggagtggga ccaggagtcg gctgtcttcc acctggagca cgcagccaac     1680
ctgggcgagc tggaggccat cgtgggcctg ggactcatgt actcgcagtt gcctcatcac     1740
atcctagccg atgtctctct gaaggagaca gaagagaaca aaaccaaagg atttgattac     1800
ttactaaagg ccgctgaagc tggcgacagg cagtccatga tcctagtggc gcgagctttt     1860
gactctggcc agaaccctca gcccggacag tgccaagact ggctagaggc cctgcactgg     1920
tacaacactg ccctggagat gacggactgt gatgagggcg gtgagtacga cggaatgcag     1980
gacgagcccc ggtacatgat gctggccagg gaggcagaga tgctgttcac aggaggctac     2040
gggctggaga aggacccgca gagatcaggg gacttgtata cccaggcagc agaggcagcg     2100
atggaagcca tgaagggccg actggccaac cagtactacc aaaaggctga agaggcctgg     2160
gcccagatgg aggaataa                                                   2178
```

<210> SEQ ID NO 2
<211> LENGTH: 725
<212> TYPE: PRT
<213> ORGANISM: Homo sapiens

<400> SEQUENCE: 2

Met Ala Asp Glu Asp Leu Ile Phe Arg Leu Glu Gly Val Asp Gly Gly
1               5                   10                  15

Gln Ser Pro Arg Ala Gly His Asp Gly Asp Ser Asp Gly Asp Ser Asp
                20                  25                  30

Asp Glu Glu Gly Tyr Phe Ile Cys Pro Ile Thr Asp Asp Pro Ser Ser
            35                  40                  45

Asn Gln Asn Val Asn Ser Lys Val Asn Lys Tyr Tyr Ser Asn Leu Thr
        50                  55                  60

Lys Ser Glu Arg Tyr Ser Ser Ser Gly Ser Pro Ala Asn Ser Phe His

```
                65                  70                  75                  80
            Phe Lys Glu Ala Trp Lys His Ala Ile Gln Lys Ala Lys His Met Pro
                             85                  90                  95

Asp Pro Trp Ala Glu Phe His Leu Glu Asp Ile Ala Thr Glu Arg Ala
                            100                 105                 110

Thr Arg His Arg Tyr Asn Ala Val Thr Gly Glu Trp Leu Asp Asp Glu
                            115                 120                 125

Val Leu Ile Lys Met Ala Ser Gln Pro Phe Gly Arg Gly Ala Met Arg
                130                 135                 140

Glu Cys Phe Arg Thr Lys Lys Leu Ser Asn Phe Leu His Ala Gln Gln
            145                 150                 155                 160

Trp Lys Gly Ala Ser Asn Tyr Val Ala Lys Arg Tyr Ile Glu Pro Val
                                165                 170                 175

Asp Arg Asp Val Tyr Phe Glu Asp Val Arg Leu Gln Met Glu Ala Lys
                            180                 185                 190

Leu Trp Gly Glu Glu Tyr Asn Arg His Lys Pro Pro Lys Gln Val Asp
                            195                 200                 205

Ile Met Gln Met Cys Ile Ile Glu Leu Lys Asp Arg Pro Gly Lys Pro
                210                 215                 220

Leu Phe His Leu Glu His Tyr Ile Glu Gly Lys Tyr Ile Lys Tyr Asn
            225                 230                 235                 240

Ser Asn Ser Gly Phe Val Arg Asp Asp Asn Ile Arg Leu Thr Pro Gln
                                245                 250                 255

Ala Phe Ser His Phe Thr Phe Glu Arg Ser Gly His Gln Leu Ile Val
                            260                 265                 270

Val Asp Ile Gln Gly Val Gly Asp Leu Tyr Thr Asp Pro Gln Ile His
                            275                 280                 285

Thr Glu Thr Gly Thr Asp Phe Gly Asp Gly Asn Leu Gly Val Arg Gly
                290                 295                 300

Met Ala Leu Phe Phe Tyr Ser His Ala Cys Asn Arg Ile Cys Glu Ser
            305                 310                 315                 320

Met Gly Leu Ala Pro Phe Asp Leu Ser Pro Arg Glu Arg Asp Ala Val
                                325                 330                 335

Asn Gln Asn Thr Lys Leu Leu Gln Ser Ala Lys Thr Ile Leu Arg Gly
                            340                 345                 350

Thr Glu Lys Cys Gly Ser Pro Arg Val Arg Thr Leu Ser Gly Ser
                            355                 360                 365

Arg Pro Pro Leu Leu Arg Pro Leu Ser Glu Asn Ser Gly Asp Glu Asn
                370                 375                 380

Met Ser Asp Val Thr Phe Asp Ser Leu Pro Ser Ser Pro Ser Ser Ala
            385                 390                 395                 400

Thr Pro His Ser Gln Lys Leu Asp His Leu His Trp Pro Val Phe Ser
                                405                 410                 415

Asp Leu Asp Asn Met Ala Ser Arg Asp His Asp His Leu Asp Asn His
                            420                 425                 430

Arg Glu Ser Glu Asn Ser Gly Asp Ser Gly Tyr Pro Ser Glu Lys Arg
                            435                 440                 445

Gly Glu Leu Asp Asp Pro Glu Pro Arg Glu His Gly His Ser Tyr Ser
                450                 455                 460

Asn Arg Lys Tyr Glu Ser Asp Glu Asp Ser Leu Gly Ser Ser Gly Arg
            465                 470                 475                 480

Val Cys Val Glu Lys Trp Asn Leu Leu Asn Ser Ser Arg Leu His Leu
                                485                 490                 495
```

```
Pro Arg Ala Ser Ala Val Ala Leu Glu Val Gln Arg Leu Asn Ala Leu
                500                 505                 510
Asp Leu Glu Lys Lys Ile Gly Lys Ser Ile Leu Gly Lys Val His Leu
            515                 520                 525
Ala Met Val Arg Tyr His Glu Gly Gly Arg Phe Cys Glu Lys Gly Glu
        530                 535                 540
Glu Trp Asp Gln Glu Ser Ala Val Phe His Leu Glu His Ala Ala Asn
545                 550                 555                 560
Leu Gly Glu Leu Glu Ala Ile Val Gly Leu Gly Leu Met Tyr Ser Gln
                565                 570                 575
Leu Pro His His Ile Leu Ala Asp Val Ser Leu Lys Glu Thr Glu Glu
            580                 585                 590
Asn Lys Thr Lys Gly Phe Asp Tyr Leu Leu Lys Ala Ala Glu Ala Gly
        595                 600                 605
Asp Arg Gln Ser Met Ile Leu Val Ala Arg Ala Phe Asp Ser Gly Gln
610                 615                 620
Asn Leu Ser Pro Asp Arg Cys Gln Asp Trp Leu Glu Ala Leu His Trp
625                 630                 635                 640
Tyr Asn Thr Ala Leu Glu Met Thr Asp Cys Asp Glu Gly Gly Glu Tyr
                645                 650                 655
Asp Gly Met Gln Asp Glu Pro Arg Tyr Met Met Leu Ala Arg Glu Ala
            660                 665                 670
Glu Met Leu Phe Thr Gly Gly Tyr Gly Leu Glu Lys Asp Pro Gln Arg
        675                 680                 685
Ser Gly Asp Leu Tyr Thr Gln Ala Ala Glu Ala Met Glu Ala Met
        690                 695                 700
Lys Gly Arg Leu Ala Asn Gln Tyr Tyr Gln Lys Ala Glu Glu Ala Trp
705                 710                 715                 720
Ala Gln Met Glu Glu
                725

<210> SEQ ID NO 3
<211> LENGTH: 2175
<212> TYPE: DNA
<213> ORGANISM: Mus musculus

<400> SEQUENCE: 3
atggcagacg aagacctcat cttctgcctg gaaggtgttg acggtggcag gtgctcccga      60
gctggccaca atgcggactc tgacacagac agtgacgatg atgagggcta tttcatctgc     120
cccatcactg atgaccacat gtccaatcag aatgtcagct ccaaagtcca gagctactat     180
agcaacctaa caaaaacaga gtgcggctcc acagggtcac cagccagctc cttccacttc     240
aaggaagcct ggaagcatgc gatcgagaaa gccaagcaca tgcctgaccc ctgggctgaa     300
ttccatctcg aggacatcgc cacagaacat gctactcggc acaggtacaa cgctgtcacc     360
ggggaatggc tgaaagacga ggttctgatc aagatggcgt ctcagccctt cggccgtgga     420
gcaatgaggg agtgcttcag gacgaagaaa ctctccaact tcttgcacgc ccagcaatgg     480
aagggggcct ccaactacgt ggccaagcgc tacatcgagc ggtggacag gagcgtgtac     540 tttgaggatg tgcagctcca gatggaggcg aagctctggg gggaggatta caatcggcac     600
aagcccccca gcaggtgga tatcatgcag atgtgcatca ttgagctaaa ggacagacca     660
ggccagcccc tcttccactt ggagcactac attgagggca gtacatcaa gtacaattcc     720 aactcaggct ttgtccgtga tgacaacatc cgactaaccc cacaggcctt cagccatttc     780
acatttgagc gttctggtca tcagctgatt gtagtggaca tccagggtgt gggtgacctt     840
```

```
tataccgacc cacagatcca cactgagaaa ggcactgact ttggagatgg taaccttggt      900
gtccggggaa tggctctctt cttctactct catgcctgca accggatttg tcagagcatg      960
ggccttacgc cctttgacct ctccccacgg aacaggatg cggtgaatca gagcaccagg     1020
ctattgcaat cagccaagac catcttgagg gggacagagg agaagtgtgg gagtccccgc     1080
ataaggacac tctctagcag ccggcccct ttgctccttc gcctgtcaga gaactccggg      1140
gatgagaaca tgagtgacgt gacctttgac tctctgcctt cctccccgtc ttcagctaca     1200
ccacacagcc agaaactgga ccacctccat tggccagtgt ttggtgacct cgataacatg     1260
ggccctagag accatgaccg tatggacaat caccgggact ctgagaatag tggggacagt     1320
gggtatccaa gcgagaagcg aagtgacctg gatgatcctg agccccgaga acacggccac     1380
tccaacggca accgaaggca tgaatctgac gaggatagcc tgggcagctc tggacgggtc     1440
tgtgtggaga cgtggaacct gctcaatccc tcccgcctgc acctgccgag gccctcggcc     1500
gtggccctag aagtgcagag gctaaatgcc ctggaccttg aaggaaaat cgggaagtct      1560
gttttgggga agtccatttt ggccatggtg cgataccacg agggcgggcg cttctgcgag     1620
aaggatgagg agtgggatcg agagtcagcc atcttccatc tggagcatgc agctgacctg     1680
ggagaactgg aggccatcgt gggcctaggc ctcatgtact ctcagctgcc ccaccacatc     1740
ctggctgatg tctctctgaa ggagacagag gagaacaaga caaaaggctt tgattactta     1800
ctgaaggcgg cagaagctgg tgacaggcat ccatgatttt tagtggcccg agcttttgac     1860
actggcctga acctcagccc agacaggtgt caagactggt cggaagcctt gcactggtac     1920
aacacagccc tggagacaac agactgcgat gaaggcgggg agtacgatgg gatacaggac     1980
gagccccagt acgcactgct ggccaggag gcggagatgc tgctcaccgg gggatttgga     2040
ctggacaaga accccaaag atcaggagat ttgtacaccc aggcagctga ggcagcaatg     2100
gaagccatga agggccggct agccaaccag tactacgaga aggcggaaga ggcctgggcc     2160
cagatggagg aataa                                                     2175
```

<210> SEQ ID NO 4
<211> LENGTH: 724
<212> TYPE: PRT
<213> ORGANISM: Mus musculus

<400> SEQUENCE: 4

Met Ala Asp Glu Asp Leu Ile Phe Cys Leu Glu Gly Val Asp Gly Gly
1               5                   10                  15

Arg Cys Ser Arg Ala Gly His Asn Ala Asp Ser Asp Thr Asp Ser Asp
            20                  25                  30

Asp Asp Glu Gly Tyr Phe Ile Cys Pro Ile Thr Asp Asp His Met Ser
        35                  40                  45

Asn Gln Asn Val Ser Ser Lys Val Gln Ser Tyr Tyr Ser Asn Leu Thr
    50                  55                  60

Lys Thr Glu Cys Gly Ser Thr Gly Ser Pro Ala Ser Ser Phe His Phe
65                  70                  75                  80

Lys Glu Ala Trp Lys His Ala Ile Glu Lys Ala Lys His Met Pro Asp
                85                  90                  95

Pro Trp Ala Glu Phe His Leu Glu Asp Ile Ala Thr Glu His Ala Thr
            100                 105                 110

Arg His Arg Tyr Asn Ala Val Thr Gly Glu Trp Leu Lys Asp Glu Val
        115                 120                 125

Leu Ile Lys Met Ala Ser Gln Pro Phe Gly Arg Gly Ala Met Arg Glu

```
                130                 135                 140
Cys Phe Arg Thr Lys Lys Leu Ser Asn Phe Leu His Ala Gln Gln Trp
145                 150                 155                 160

Lys Gly Ala Ser Asn Tyr Val Ala Lys Arg Tyr Ile Glu Pro Val Asp
                165                 170                 175

Arg Ser Val Tyr Phe Glu Asp Val Gln Leu Gln Met Glu Ala Lys Leu
                180                 185                 190

Trp Gly Glu Asp Tyr Asn Arg His Lys Pro Pro Lys Gln Val Asp Ile
                195                 200                 205

Met Gln Met Cys Ile Ile Glu Leu Lys Asp Arg Pro Gly Gln Pro Leu
210                 215                 220

Phe His Leu Glu His Tyr Ile Glu Gly Lys Tyr Ile Lys Tyr Asn Ser
225                 230                 235                 240

Asn Ser Gly Phe Val Arg Asp Asp Asn Ile Arg Leu Thr Pro Gln Ala
                245                 250                 255

Phe Ser His Phe Thr Phe Glu Arg Ser Gly His Gln Leu Ile Val Val
                260                 265                 270

Asp Ile Gln Gly Val Gly Asp Leu Tyr Thr Asp Pro Gln Ile His Thr
                275                 280                 285

Glu Lys Gly Thr Asp Phe Gly Asp Gly Asn Leu Gly Val Arg Gly Met
290                 295                 300

Ala Leu Phe Phe Tyr Ser His Ala Cys Asn Arg Ile Cys Gln Ser Met
305                 310                 315                 320

Gly Leu Thr Pro Phe Asp Leu Ser Pro Arg Glu Gln Asp Ala Val Asn
                325                 330                 335

Gln Ser Thr Arg Leu Leu Gln Ser Ala Lys Thr Ile Leu Arg Gly Thr
                340                 345                 350

Glu Glu Lys Cys Gly Ser Pro Arg Ile Arg Thr Leu Ser Ser Ser Arg
                355                 360                 365

Pro Pro Leu Leu Leu Arg Leu Ser Glu Asn Ser Gly Asp Glu Asn Met
370                 375                 380

Ser Asp Val Thr Phe Asp Ser Leu Pro Ser Ser Pro Ser Ser Ala Thr
385                 390                 395                 400

Pro His Ser Gln Lys Leu Asp His Leu His Trp Pro Val Phe Gly Asp
                405                 410                 415

Leu Asp Asn Met Gly Pro Arg Asp Asp Arg Met Asp Asn His Arg
                420                 425                 430

Asp Ser Glu Asn Ser Gly Asp Ser Gly Tyr Pro Ser Glu Lys Arg Ser
                435                 440                 445

Asp Leu Asp Asp Pro Glu Pro Arg Glu His Gly His Ser Asn Gly Asn
450                 455                 460

Arg Arg His Glu Ser Asp Glu Asp Ser Leu Gly Ser Ser Gly Arg Val
465                 470                 475                 480

Cys Val Glu Thr Trp Asn Leu Leu Asn Pro Ser Arg Leu His Leu Pro
                485                 490                 495

Arg Pro Ser Ala Val Ala Leu Glu Val Gln Arg Leu Asn Ala Leu Asp
                500                 505                 510

Leu Gly Arg Lys Ile Gly Lys Ser Val Leu Gly Lys Val His Leu Ala
                515                 520                 525

Met Val Arg Tyr His Glu Gly Gly Arg Phe Cys Glu Lys Asp Glu Glu
                530                 535                 540

Trp Asp Arg Glu Ser Ala Ile Phe His Leu Glu His Ala Ala Asp Leu
545                 550                 555                 560
```

-continued

```
Gly Glu Leu Glu Ala Ile Val Gly Leu Gly Leu Met Tyr Ser Gln Leu
            565                 570                 575

Pro His His Ile Leu Ala Asp Val Ser Leu Lys Glu Thr Glu Glu Asn
            580                 585                 590

Lys Thr Lys Gly Phe Asp Tyr Leu Leu Lys Ala Ala Glu Ala Gly Asp
            595                 600                 605

Arg His Ser Met Ile Leu Val Ala Arg Ala Phe Asp Thr Gly Leu Asn
            610                 615                 620

Leu Ser Pro Asp Arg Cys Gln Asp Trp Ser Glu Ala Leu His Trp Tyr
625                 630                 635                 640

Asn Thr Ala Leu Glu Thr Thr Asp Cys Asp Gly Gly Glu Tyr Asp
            645                 650                 655

Gly Ile Gln Asp Glu Pro Gln Tyr Ala Leu Leu Ala Arg Glu Ala Glu
            660                 665                 670

Met Leu Leu Thr Gly Gly Phe Gly Leu Asp Lys Asn Pro Gln Arg Ser
            675                 680                 685

Gly Asp Leu Tyr Thr Gln Ala Ala Glu Ala Ala Met Glu Ala Met Lys
            690                 695                 700

Gly Arg Leu Ala Asn Gln Tyr Tyr Glu Lys Ala Glu Glu Ala Trp Ala
705                 710                 715                 720

Gln Met Glu Glu
```

METHODS AND MEANS FOR INCREASING RESISTANCE TO CELL DAMAGE

CROSS-REFERENCE TO RELATED APPLICATIONS

This application is a continuation-in-part of International Application No. PCT/US2005/022741, filed Jun. 24, 2005, which claims priority to U.S. Provisional Application Ser. No. 60/582,411, which was filed on Jun. 24, 2004; and also claims priority under 35 U.S.C. §119(e) to U.S. Provisional Application Ser. No. 60/819,688, which was filed on Jul. 10, 2006, the disclosures of all three of which are incorporated herein by reference.

STATEMENT REGARDING FEDERALLY SPONSORED RESEARCH

The U.S. Government has a paid-up license in this invention and the right in limited circumstances to require the patent owner to license others on reasonable terms as provided for by the terms of grant R01AG19890 awarded by the U.S. National Institutes of Health (National Institute on Aging).

FIELD OF THE INVENTION

The present invention relates to the field of cell damage and the development of compositions and methods to increase resistance to cell damage. In particular, the invention relates to the manipulation of the elongation factor 2 (eEF2) kinase in order to increase resistance to cell damage and increase life span of cells.

BACKGROUND OF THE INVENTION

Accumulation of damaged cellular proteins is postulated to be a major contributor to aging and sensitivity to cell damage. Decreases in both protein synthesis and degradation rates may result in the persistence of defective or modified proteins and thus the overall rate of protein turnover can affect the cells' response to cell damage.

Elongation factor-2 kinase (eEF2 kinase) is a ubiquitous protein kinase that belongs to the alpha-kinase family of protein kinases. these protein kinases do not display sequence homology to conventional eukaryotic protein kinases (Ryazanov, A. G. et al. *Proc. Natl. Acad. Sci. USA* 94, 4884-4889 (1997); Ryazanov, A. G., Pavur, K. S., Dorovkov, M. V. *Curr. Biol.* 28, 943-945 (1999); and Ryazanov, A. G. *FEBS Lett.* 514, 26-29 (2002)). The only known substrate of eEF2 kinase is eEF2, the protein that promotes ribosomal translocation during the elongation phase of protein synthesis. eEF2 is inactivated upon phosphorylation by eEF2 kinase, implying that the phosphorylation process catalyzed by eEF2 kinase can be a mechanism of protein synthesis regulation at the elongation stage (Ryazanov, A. G., et al. *Nature* 334, 170-173 (1988)). eEF2 kinase is a highly specific protein kinase, which phosphorylates and inactivates elongation factor-2 (Ryazanov, A. G., et al. *Nature* 324, 170-173 (1988); and Ryazanov, A. G. et al. *Proc. Natl. Acad. Sci. U.S.A.* 94, 4884-4889 (1997)). This kinase is regulated by the IGF-1/mTOR pathway and is implicated in the control of the global rate of protein synthesis at the elongation stage (Browne, G. J., Proud C. G. *Eur. J. Biochem.* 269, 5360-5368 (2002); and Proud C. G. *Curr. Top. Microbiol. Immunol.* 279, 215-244 (2004)). eEF2 kinase activity in cells is normally low, but is stimulated by various stress-inducing agents such as $Ca^{2+}$ ionophores, acidic pH and hydrogen peroxide (Nairn, A. C. and Palfrey, H. C. *Cold Spring Harbor Laboratory Press*, 295-318 (1996); Patel, J. et al., *Eur. J. Biochem.* 269, 3076-3085 (2002); and Dorovkov, M. V., et al. *Biochemistry* 41, 13444-13450 (2002)).

To uncover the physiological role of eEF2K eEF2K knockout mice are prepared. Despite a complete lack of eEF2K activity, eEF2K knockout mice have normal development, behavior and reproduction. Moreover, these mice have increased lifespan. However, fibroblasts from eEF2K knockout mice are found to be resistant to various cytotoxic agents. The effect of eEF2K knockout on cell resistance to cytotoxic agents may depend on functional p53 since it is abolished in cells in which p53 is inactivated. Intriguingly, knockout mice have significantly extended maximal lifespan. These findings suggest that eEF2K is a modulator of stress resistance and aging, and that its inactivation could protect cells from stress-induced injury and increase life span in mammals.

One of the hallmarks of aging is the progressive decline in the rate of protein synthesis and degradation. This decline in protein turnover can be a major factor contributing to an increase in the concentration of damaged proteins with age. Therefore, by regulating the overall rate of protein synthesis and/or degradation it might be possible to modulate the rate of aging. Since knockout of eEF2 kinase increases maximal life span in mice, manipulation of expression or activity if eEF2 kinase may offer a therapeutic basis for regulating protein turnover and reducing cell damage due to stress, exposure to chemotherapeutic agents, and other factors.

SUMMARY OF THE INVENTION

In accordance with the present invention, it has now been shown for the first time that a decrease in activity of eEF2 kinase causes an increase in overall protein turnover in cells, the result being increased resistance to cell damage, particularly stress-induced cell damage. Since the same enzyme is present in all animals, including humans, it is now clearly predictable that increasing protein turnover in cells, particularly through the inhibition of this enzyme, in human and animal subjects will result in decreasing cell death. The discoveries made in accordance with the present invention enable a variety of useful methods, kits and pharmaceutical formulations directed to increasing resistance to cell damage in the cells of a subject, thereby decreasing cell death.

According to one aspect of the invention, methods are provided to increase resistance to cell damage in a subject. These methods comprise increasing protein turnover in the subject, the increase in protein turnover resulting in the increased resistance to cell damage of the subject. Preferably, the protein turnover in the subject is accomplished by decreasing activity of eEF2 kinase in the subject. In one embodiment, the eEF2 kinase activity is decreased by decreasing the amount of functional eEF2 kinase produced by the subject. In a preferred embodiment the amount of functional eEF2 kinase is decreased by decreasing eEF2 kinase activity in the cell, preferably by contacting the eEF2 kinase with a compound that inhibits phosphorylation of eEF2. In another preferred embodiment, the amount of functional eEF2 kinase is decreased by reducing expression of a gene encoding the eEF2 kinase. Alternatively, the amount of functional eEF2 kinase is decreased by altering a gene encoding the eEF2 kinase such that the gene encodes a dysfunctional or non-functional eEF2 kinase.

According to another aspect of the invention, a genetically manipulated non-human organism is provided, in which an enzyme that negatively regulates protein synthesis is dysfunctional, non-functional or absent. Preferably, the organism is a rodent, preferably a mouse and the enzyme is eEF2 kinase. Another aspect of the present invention relates to vector constructs useful in the construction of genetically manipulated non-human organism, in which eEF2 kinase is dysfunctional, non-functional or absent.

According to another aspect of the invention, a pharmaceutical formulation for increasing resistance to cell damage of a subject is provided. The formulation comprises an agent that increases cellular protein turnover in a biologically compatible medium. Preferably, the formulation comprises an inhibitor of eEF2 activity or gene expression.

Various diagnostic and prognostic assays and kits are also provided in accordance with the present invention, as described in greater detail below. Other features and advantages of the present invention will be understood by reference to the drawings, detailed description and examples that follow.

```
                                    (SEQ ID NO: 5)
5'-TGC GAG GCC AGA GGC CAC TTG TGT AGC-3',

SA8:
                                    (SEQ ID NO: 6)
5'-GGC CGG CTG CTA GAG AGT GTC-3',

SA5:
                                    (SEQ ID NO: 7)
5'-CAT CAG CTG ATT GTA GTG GAC ATC-3').
```

Figure 3:
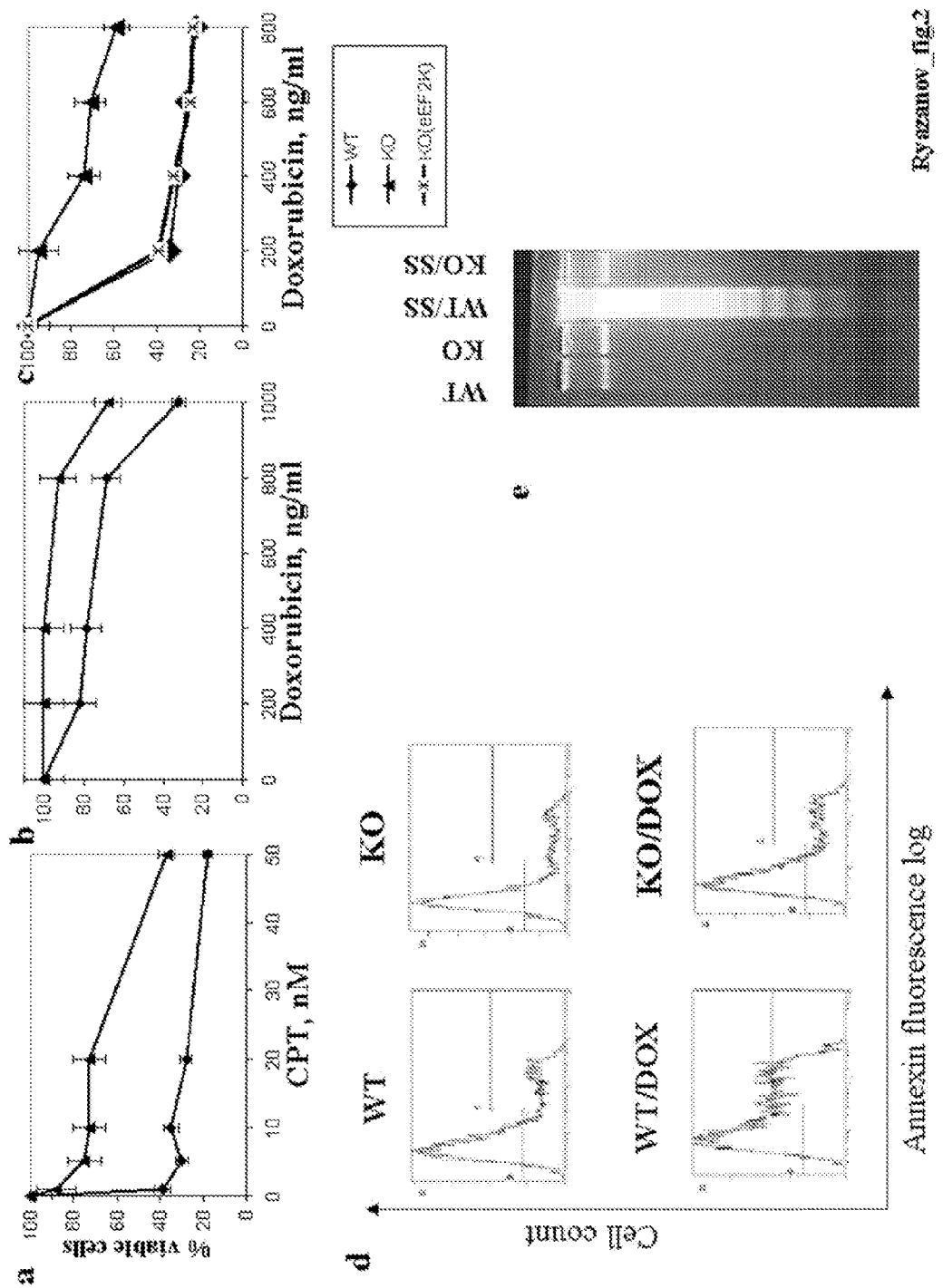

FIG. 3. eEF2 kinase deficiency increases the resistance of mouse embryonic fibroblasts to chemotherapeutic drugs. a, b. Graphs representing the response of eEF2+/+ (WT) and eEF2K−/− (KO) MEFs to CPT and DOX, measured by MTT assay. Cells are incubated for 24 h at indicated concentrations of a drug. c. Graphs of MTT assay comparing the response of eEF2K+/+, eEF2K−/− and KO (eEF2K)(cell line, transfected with cDNA of eEF2K) to doxorubicin. Experiment performed as described in a, b. d. Flow cytometric analysis of eEF2K+/+ and eEF2K−/− MEFs treated with 600 ng/ml of DOX for 24 h. e. Analysis of apoptotic DNA fragmentation in wild type and eEF2K−/− stable cell lines in response to a serum starvation (SS) for 48 h.

Figure 4:
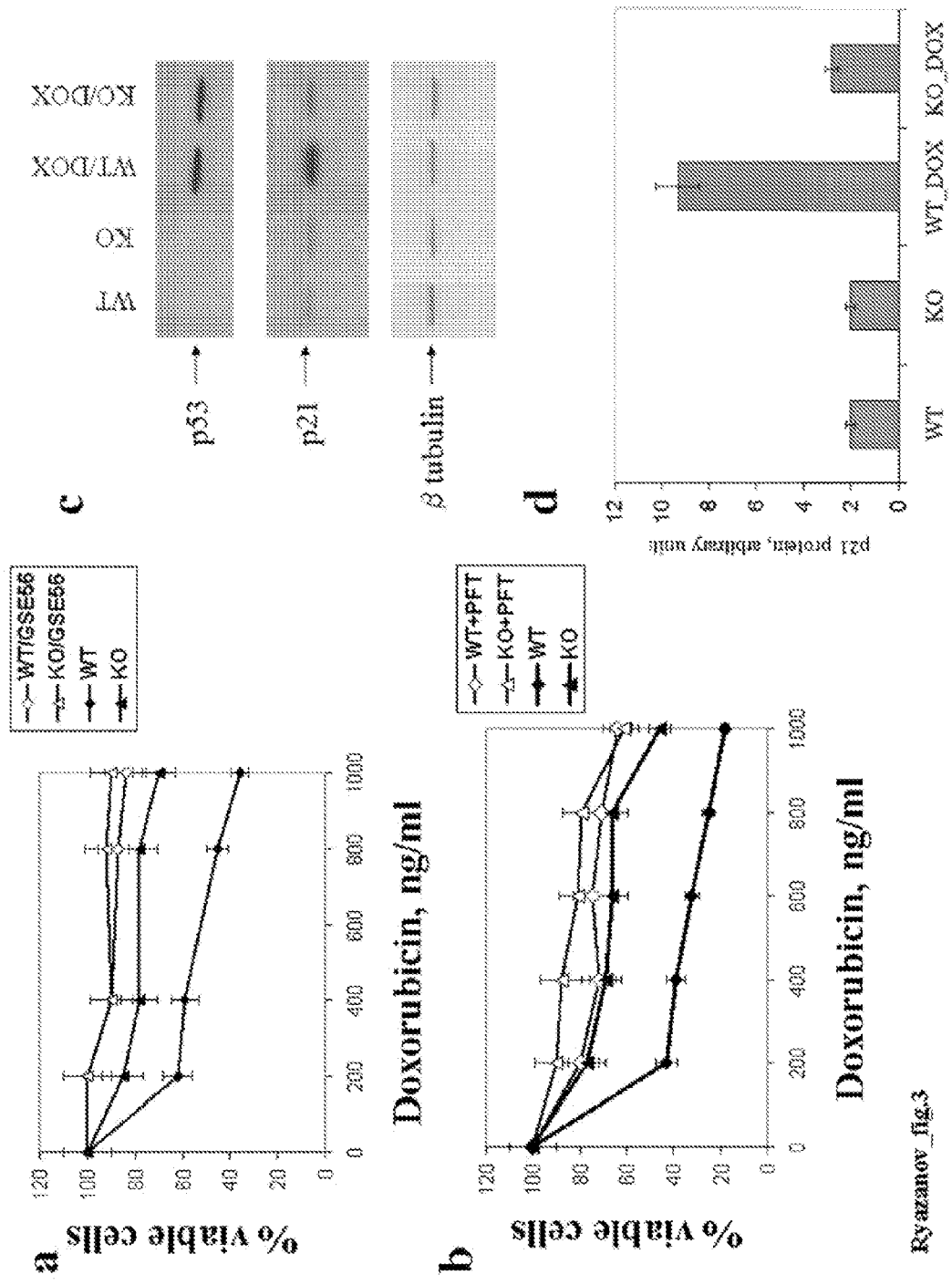

FIG. 4. Effect of eEF2 kinase knockout on drug resistance depends on functional p53. a. Drug sensitivity assay of eEF2K+/+ and eEF2K−/− stable cell lines and the same cell lines expressing dominant-negative p53 mutant GSE56. Cells are treated with indicated concentrations of DOX and after 24 h cell viability is measured by MTT assay. b. Drug sensitivity assay of eEF2K+/+ and eEF2K−/− stable cell lines and the same cell lines treated with PFT α. MTT assay is done as described in a. c. Western blot analysis of p53, p21 and β tubulin expression in wild type and eEF2K−/− MEFs after DOX treatment. d. Quantification of the amount of p21 protein before and after incubation with DOX.

Figure 5:
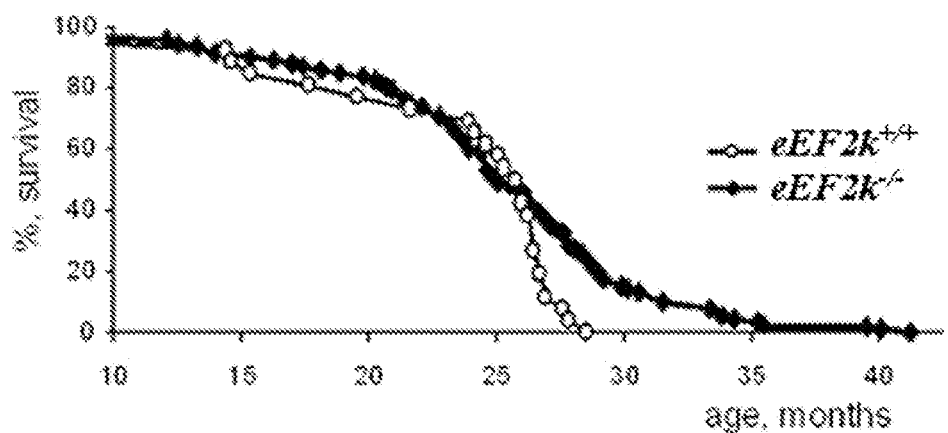
Figure 5:
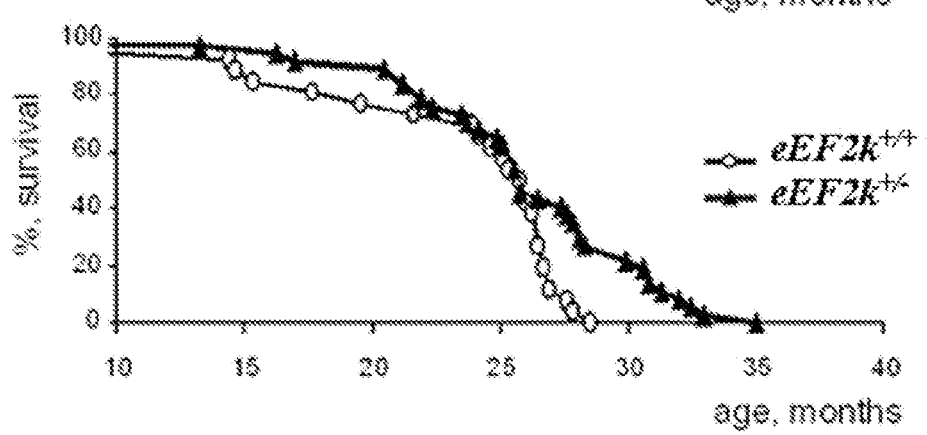
Figure 5:
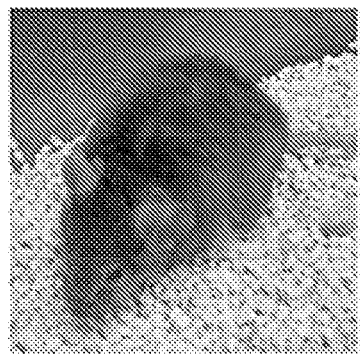

FIG. 5. Knockout of eEF2 kinase leads to increased maximal life span in mice. a. Comparison of survival curves of eEF2k−/− (diamonds, n=82) and eEF2k+/+ (circles, n=32) mice. b. Comparison of survival curves of eEF2k+/− (triangles, n=38) and eEF2k+/+ (circles, n=32) mice. c. 40 months old eEF2k−/− mouse.

Figure 6:
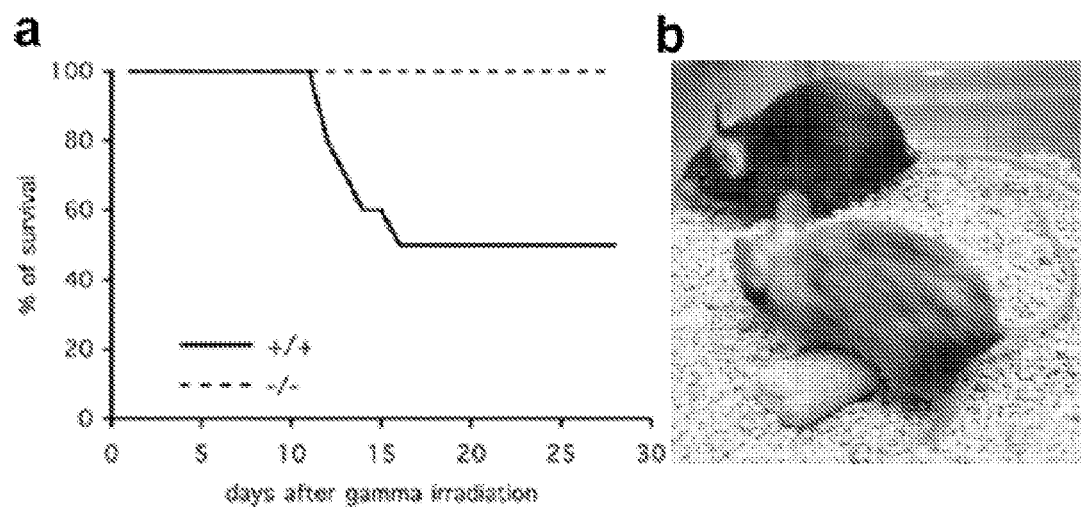

FIG. 6. eEF2K−/− mice are resistant to gamma irradiation. a. The survival of mice after whole-body gamma irradiation. Mice at 8 to 12 weeks of age are exposed to 8 Gy of whole-body γ-irradiation and survival is monitored daily. Each cohort contains 10 mice including 5 males and 5 females. b. The appearances of eEF2K+/+ mice (bottom) and eEF2K−/− mice (top) one month after 8 Gy of γ-irradiation.

Figure 7:
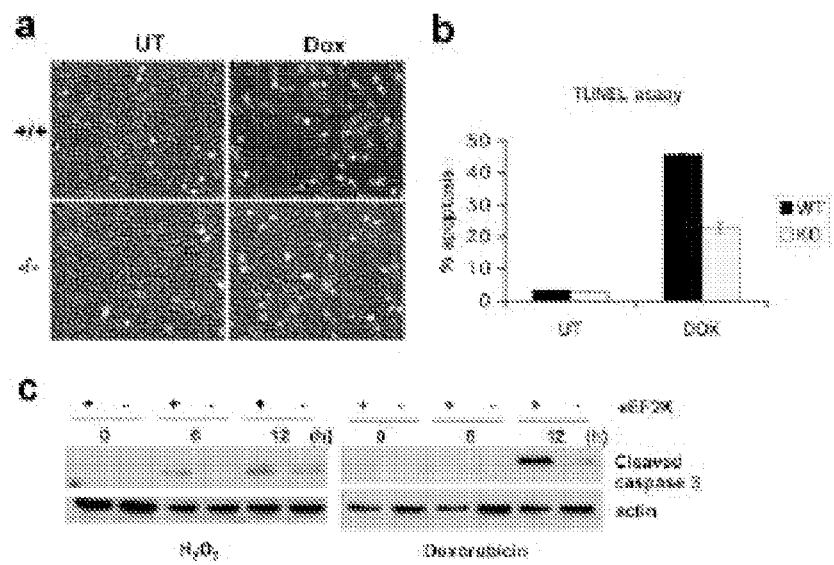

FIG. 7. eEF2K−/− cells are resistant to apoptosis. a. Phase-contrast images of cells. MEFs are treated with 1.6 μM of doxorubicin for 24 hours. b. TUNEL assay of MEFs treated with 1.6 μM of doxorubicin for 12 hours. Apoptotic cells are analyzed by flow cytometry. c. The effect of introduction of eEF2K cDNA into eEF2K−/− MEFs on the activation of caspase 3 induced by 0.8 μM of doxorubicin or 600 μM of $H_2O_2$. Activation of caspase 3 is analyzed by western blotting.

Figure 8:
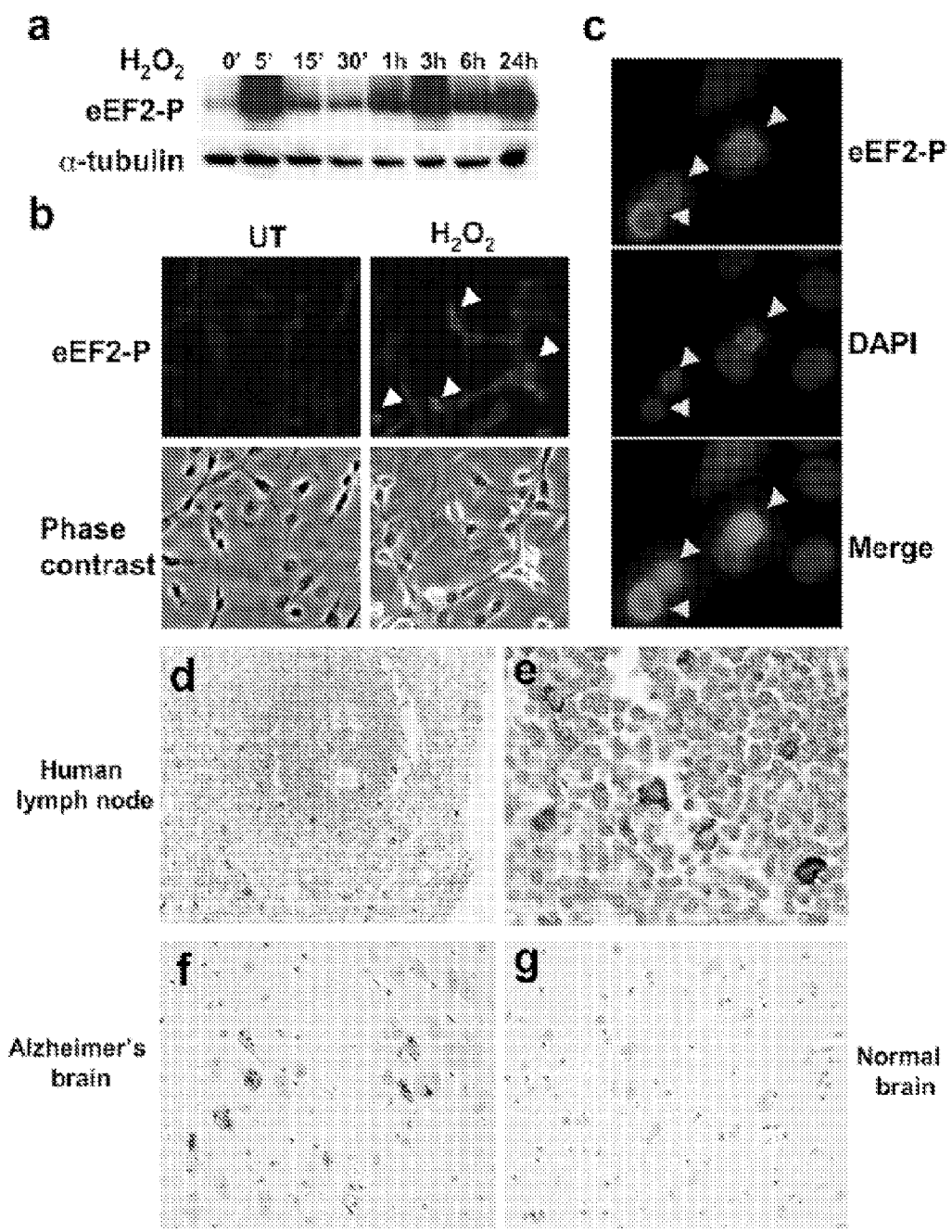

FIG. 8. Phosphorylation of eEF2 occurs in cells undergoing apoptosis. a. Western blot analysis of phosphorylated eEF2. NIH3T3 cells are exposed to 80 μM of hydrogen peroxide for the indicated time periods and eEF2 phosphorylation is analyzed by western blotting using antibodies specific for phosphorylated eEF2. b. Immunostaining of phosphorylated eEF2 in NIH3T3 cells. Cells are exposed to 400 μM of $H_2O_2$ for 3 hours and phosphorylated eEF2 is detected by immunostaining in both $H_2O_2$-treated and untreated (UT) cells. Cells showing the highest phosphorylated eEF2 levels are indicated by the white arrowheads. c. HeLa cells are treated with 400 μM of $H_2O_2$ for 3 hours and immunostaining is performed. Cells with condensed chromatin are indicated by gray arrowheads. d, e, f, g. immunostaining of phosphorylated eEF2 in human lymph nodes and brain. e. higher magnification of d.

DETAILED DESCRIPTION OF THE INVENTION

The present invention is based in part on the discovery that decreasing eEF2 kinase activity in a cell results in an increase in resistance to damage to the cell, as well as a resistance to programmed cell death (apoptosis). Without being bound by any particular theory, it is believed that the increased levels of protein translation and protein turnover that result from a decrease in eEF2 kinase activity help protect cells from damage and subsequent death. The term "protein turnover" is art-recognized and refers to the coordinated synthesis and degradation of proteins that occurs in living cells, tissues and organisms.

Cell Death

Apoptosis is referred to as a process of "programmed cell death." During normal somatic development, cell populations in specific organs or tissues may be programmed for death as part of the developmental progression of tissue remodeling or obsolescence. See J. J. Cohen, Avd. Immunol. 50:55-85 (1991); M. Baringa, Science 259:762-3 (1993). Apoptosis is internally triggered by biochemical or biomolecular mechanisms intrinsic to the cell cycle, resulting in an activation of endogenous endonucleases (enzymes that degrade DNA), leading to DNA strand breaks between nucleosomes and degradation of the genomic DNA by fragmentation. A. H. Wyllie, Nature 284:555-6 (1980). Apoptosis in mature tissues occurs in normal processes such as inflammation or rejuvenation. M. Schmied et al., Am. J. Pathol. 143:446-52 (1993); Abnormal clonal proliferations in immunologic diseases or malignancies may be related to a failure of normal apoptosis. J. Marx, Science 259:760-1 (1993).

The relationship of apoptosis and/or cell damage to the cell cycle, including checkpoint controls, during cancer chemotherapy is a subject of interest to oncologists and molecular biologists. See T. Shimizu et al., Cancer Res. 55:228-231 (1995); O'Connor, supra. (1992). The expression of p53 in damaged cells is one factor in determining the course of divergent biochemical pathways, which can lead to either DNA repair or apoptosis. E Yonish-Rouach et al., Mol Cell Biol 13:1415-23 (1993); D E Fisher, Cell 78:539-542 (1994).

In chemotherapy for malignancy, treatments with targeted cytotoxic effect have involved a number clinical considerations: they may be used in the primary effort to control cancer (induction chemotherapy), or as an adjunct to surgery or radiotherapy (adjuvant chemotherapy). DeVita, supra (1994). Local treatments have included infusion of a targeted cytotoxic compound into body cavities to control the spread of malignancies such as breast or ovarian cancers.

Cell Damage

Cell damage is caused by a treatment that causes stress to the cell. In a particularly preferred embodiment. Stress may be caused by a variety of factors, including increased acidity, oxidative stress, or exposure of the cell to a compound used for treatment of a disease state, such as for example, camptothecin (CPT), doxorubicin (DOX), or taxol. Cell damage may also stem from ionizing radiation, ultraviolet radiation and free radicals.

Decreasing Kinase Activity

The present invention relates to a method of reducing damage to a cell or increasing resistance to damage to a cell, comprising decreasing eEF2 kinase activity in the cell. The cell may be in cultures, in a tissue or in a subject in need of treatment. The subject may be a mammal such as a human.

The term "inhibition" refers to the reduction or down regulation of a process or activity that results in the absence or minimization of that process or activity. The term "inhibit" or "inhibiting", in relationship to the term "activity" means that an activity is decreased or prevented in the presence of a compound as opposed to in the absence of the compound.

In a preferred embodiment, the decrease in eEF2 kinase activity, is accomplished by contacting the eEF kinase with a compound that decreases phosphorylation of eEF2 by the eEF2 kinase.

The term "contact" or "contacting" means bringing at least two moieties together, whether in an in vitro system or an in vivo system.

Compounds

The term "compound" is used herein in the context of a "test compound" or a "drug candidate compound" described in connection with the assays of the present invention. As such, these compounds comprise organic or inorganic compounds, derived synthetically or from natural sources. The compounds include inorganic or organic compounds such as polynucleotides, lipids or hormone analogs that are characterized by relatively low molecular weights. Other biopolymeric organic test compounds include peptides comprising from about 2 to about 40 amino acids and larger polypeptides comprising from about 40 to about 500 amino acids, such as antibodies or antibody conjugates.

Assays to Identify Compounds

There are a variety of methods that may be used to identify compounds capable of inhibition of the activity of eEF2 kinase. The affinity of the compounds to eEF2 kinase may be determined in an experiment that detects changed reaction conditions after phosphorylation of eEF2. eEF2 kinase is incubated with eEF2 and ATP in an appropriate buffer. The combination of these components results in the in vitro phosphorylation of eEF2. Sources of compounds include any commercially available screening library, peptides in a phage display library or an antibody fragment library, and compounds that have been demonstrated to have binding affinity for eEF2 kinase.

The term "binding affinity" is a property that describes how strongly two or more compounds associate with each other in a non-covalent relationship. Binding affinities can be characterized qualitatively, (such as "strong", "weak", "high", or "low") or quantitatively (such as measuring the $K_D$).

eEF2 kinase can be prepared in a number of ways depending on whether the assay will be run using cells, cell fractions or biochemically, on purified protein. eEF2 kinase can be applied as complete a polypeptides or as a polypeptide fragment, which still comprises eEF2 kinase catalytic activity.

The term "assay" means any process used to measure a specific property of a compound. A "screening assay" means a process used to characterize or select compounds based upon their activity from a collection of compounds.

The term "polypeptide" relates to proteins, proteinaceous molecules, fractions of proteins peptides and oligopeptides.

Identification of small molecules inhibiting the activity of the eEF2 kinase is performed by measuring changes in levels of phosphorylated eEF2 kinase substrate, which can be a peptide or a full-length protein, or ATP. A preferred substrate is eEF2. Since ATP is consumed during the phosphorylation of eEF2 kinase substrate, its levels correlate with the kinase activity. Measuring ATP levels via chemiluminescent reactions therefore represents a method to measure kinase activity in vitro (Perkin Elmer). In a second type of assay, changes in the levels of phosphorylated eEF2 kinase substrate are detected with phosphospecific agents and are correlated to eEF2 kinase activity. These levels are detected in solution or after immobilization of the substrate on a microtiter plate or other carrier. In solution, the phosphorylated eEF2 kinase substrate is detected via fluorescence resonance energy transfer (FRET) between the Eu labeled substrate and an APC labeled phosphospecific antibody (Perkin Elmer), via fluorescence polarization (FP) after binding of a phosphospecific antibody to the fluorescently labeled phosphorylated eEF2 kinase substrate, via an Amplified Luminescent Proximity Homogeneous Assay (ALPHA) using the phosphorylated eEF2 kinase substrate and phosphospecific antibody, both coupled to ALPHA beads (Perkin Elmer) or using the IMAP binding reagent that specifically detects phosphate groups and thus alleviates the use of the phosphospecific antibody (Molecular Devices). Alternatively, the eEF2 kinase substrate is immobilized directly or by using biotin-streptavidin on a microtiter plate. After immobilization, the level of phosphorylated eEF2 kinase substrate is detected using a classic ELISA where binding of the phosphospecific antibody is either monitored via an enzyme such as horseradish peroxidase (HRP) or alkaline phosphatase (AP) which are either directly coupled to the phosphospecific antibody or are coupled to a secondary antibody. Enzymatic activity correlates to phosphorylated eEF2 kinase substrate levels. Alternatively, binding of the Eu-labeled phosphospecific antibody to the immobilized phosphorylated eEF2 kinase substrate is determined via time resolved fluorescence energy (TRF) (Perkin Elmer). In addition, the eEF2 kinase substrate can be coated on FLASH plates (Perkin Elmer) and phosphorylation of the eEF2 kinase substrate is detected using $^{33}$P labeled ATP or $^{125}$I labeled phosphospecific antibody.

The term "agent" means any molecule, including polypeptides, polynucleotides and small molecules.

Small molecules are randomly screened or are preselected based upon drug class, (i.e. known kinase inhibitors), or upon virtual ligand screening (VLS) results. VLS uses virtual docking technology to test large numbers of small molecules in silico for their binding to the polypeptide of the invention. Small molecules are added to the kinase reaction and their effect on levels of phosphorylated eEF2 is measured with one or more of the above-described technologies.

Small molecules that inhibit the kinase activity are identified and are subsequently tested at different concentrations. IC$_{50}$ values are calculated from these dose response curves. Strong binders have an IC$_{50}$ in the nanomolar and even picomolar range.

Reduction in eEF2 Gene Expression

In another preferred embodiment, the present invention relates to a method of reducing damage to a cell or increasing resistance to damage to a cell, comprising decreasing eEF2 kinase activity by reducing the expression of a gene encoding the eEF2 kinase. This reduction in expression can be accomplished by a variety of methods and in preferred embodiments it is accomplished by altering the gene such that the gene encodes a dysfunctional or non-functional eEF2 kinase.

The term "expression" comprises both endogenous expression and overexpression by transduction.

A variety of means are available for altering a gene to effect expression. In a special embodiment the expression of a gene encoding the eEF2 kinase is reduced by contacting the gene, or an mRNA transcribed from the gene, with a compound comprising a polynucleotide selected from the group consisting of an antisense oligonucleotide, a ribozyme, a small interfering RNA (siRNA), and a short hairpin RNA (shRNA). In certain embodiments the compound comprises a polynucleotide comprising a nucleotide sequence complementary to a nucleotide sequence encoding a polypeptide comprising the amino acid sequence of SEQ ID NO: 2, (eEF2 kinase polypeptide sequence). In a particularly preferred embodiment the compound comprises a nucleotide sequence complementary to a nucleotide sequence comprising the nucleotide sequence of SEQ ID NO: 1 (eEF2 kinase polynucleotide sequence).

The term "polynucleotide" means a polynucleic acid, in single or double stranded form, and in the sense or antisense orientation, complementary polynucleic acids that hybridize to a particular polynucleic acid under stringent conditions, and polynucleotides that are homologous in at least about 60 percent of its base pairs, and more preferably 70 percent of its base pairs are in common, most preferably 90 percent, and in a special embodiment 100 percent of its base pairs. The polynucleotides include polyribonucleic acids, polydeoxyribonucleic acids, and synthetic analogues thereof. The polynucleotides are described by sequences that vary in length, that range from about 10 to about 5000 bases, preferably about 100 to about 4000 bases, more preferably about 250 to about 2500 bases. A preferred polynucleotide embodiment comprises from about 10 to about 30 bases in length. A special embodiment of polynucleotide is the polyribonucleotide of from about 10 to about 22 nucleotides, more commonly described as small interfering RNAs (siRNAs). Another special embodiment are nucleic acids with modified backcartilages such as peptide nucleic acid (PNA), polysiloxane, and 2'-O-(2-methoxy)ethylphosphorothioate, or including non-naturally occurring nucleic acid residues, or one or more nucleic acid substituents, such as methyl-, thio-, sulphate, benzoyl-, phenyl-, amino-, propyl-, chloro-, and methanocarbanucleosides, or a reporter molecule to facilitate its detection.

The term "antisense nucleic acid" refers to an oligonucleotide that has a nucleotide sequence that interacts through base pairing with a specific complementary nucleic acid sequence involved in the expression of the target such that the expression of the gene is reduced. Preferably, the specific nucleic acid sequence involved in the expression of the gene is a genomic DNA molecule or mRNA molecule that encodes (a part of) the gene. This genomic DNA molecule can comprise regulatory regions of the gene, or the coding sequence for the mature gene.

The term 'complementary to a nucleotide sequence' in the context of antisense oligonucleotides and methods should be understood as sufficiently complementary to such a sequence as to allow hybridization to that sequence in a cell, i.e., under physiological conditions.

The term "hybridization" means any process by which a strand of nucleic acid binds with a complementary strand through base pairing. The term "hybridization complex" refers to a complex formed between two nucleic acid sequences by virtue of the formation of hydrogen bonds between complementary bases. A hybridization complex may be formed in solution (e.g., C0t or R0t analysis) or formed between one nucleic acid sequence present in solution and another nucleic acid sequence immobilized on a solid support (e.g., paper, membranes, filters, chips, pins or glass slides, or any other appropriate eEF2 to which cells or their nucleic acids have been fixed). The term "stringent conditions" refers to conditions that permit hybridization between polynucleotides and the claimed polynucleotides. Stringent conditions can be defined by salt concentration, the concentration of organic solvent, e.g., formamide, temperature, and other conditions well known in the art. In particular, reducing the concentration of salt, increasing the concentration of formamide, or raising the hybridization temperature can increase stringency.

Antisense

The down regulation of gene expression using antisense nucleic acids can be achieved at the translational or transcriptional level using an expression-inhibitory agent. Antisense nucleic acids of the invention are preferably nucleic acid fragments capable of specifically hybridizing with all or part of a nucleic acid encoding a eEF2 kinase or the corresponding messenger gene or mRNA. In addition, antisense nucleic acids may be designed which decrease expression of the nucleic acid sequence capable of encoding a eEF2 kinase by inhibiting splicing of its primary transcript. Any length of antisense sequence is suitable for practice of the invention so long as it is capable of down-regulating or blocking expression of a nucleic acid coding for eEF2 kinase. Preferably, the antisense sequence is at least about 17 nucleotides in length. The preparation and use of antisense nucleic acids, DNA encoding antisense RNAs and the use of oligo and genetic antisense is known in the art.

The term "expression inhibitory agent" means a polynucleotide designed to interfere selectively with the transcription, translation and/or expression of a specific polypeptide or protein normally expressed within a cell. More particularly, "expression inhibitory agent" comprises a DNA or RNA molecule that contains a nucleotide sequence identical to or complementary to at least about 17 sequential nucleotides within the polyribonucleotide sequence coding for a specific polypeptide or protein. Exemplary expression inhibitory molecules include ribozymes, double stranded siRNA molecules, self-complementary single-stranded siRNA molecules, genetic antisense constructs, and synthetic RNA antisense molecules with modified stabilized backbones.

One embodiment of expression-inhibitory agent is a nucleic acid that is antisense to a nucleic acid comprising SEQ ID NO: 1. For example, an antisense nucleic acid (e.g. DNA) may be introduced into cells in vitro, or administered to a subject in vivo, as gene therapy to inhibit cellular expression of nucleic acids comprising SEQ ID NO: 1. Antisense oligonucleotides preferably comprise a sequence containing from about 17 to about 100 nucleotides and more preferably the antisense oligonucleotides comprise from about 18 to about 30 nucleotides. Antisense nucleic acids may be prepared from about 10 to about 30 contiguous nucleotides complementary to a nucleic acid sequence selected from the sequences of SEQ ID NO: 1.

The antisense nucleic acids are preferably oligonucleotides and may consist entirely of deoxyribo-nucleotides, modified deoxyribonucleotides, or some combination of both. The antisense nucleic acids can be synthetic oligonucleotides. The oligonucleotides may be chemically modified, if desired, to improve stability and/or selectivity. Since oligonucleotides are susceptible to degradation by intracellular nucleases, the modifications can include, for example, the use of a sulfur group to replace the free oxygen of the phosphodiester bond. This modification is called a phosphorothioate linkage. Phosphorothioate antisense oligonucleotides are water soluble, polyanionic, and resistant to endogenous nucleases. In addition, when a phosphorothioate antisense oligonucleotide hybridizes to its mRNA target, the RN202-315NA duplex activates the endogenous enzyme ribonuclease (RNase) H, which cleaves the mRNA component of the hybrid molecule.

In addition, antisense oligonucleotides with phosphoramidite and polyamide (peptide) linkages can be synthesized. These molecules should be very resistant to nuclease degradation. Furthermore, chemical groups can be added to the 2' carbon of the sugar moiety and the 5 carbon (C-5) of pyrimidines to enhance stability and facilitate the binding of the antisense oligonucleotide to its TARGET site. Modifications may include 2'-deoxy, O-pentoxy, O-propoxy, O-methoxy, fluoro, methoxyethoxy phosphorothioates, modified bases, as well as other modifications known to those of skill in the art.

Ribozyme

Another type of expression-inhibitory agent that reduces the levels of mRNA is the ribozyme. Ribozymes are catalytic RNA molecules (RNA enzymes) that have separate catalytic and substrate binding domains. The substrate binding sequence combines by nucleotide complementarity and, possibly, non-hydrogen bond interactions with its mRNA sequence. The catalytic portion cleaves the mRNA at a specific site. The substrate domain of a ribozyme can be engineered to direct it to a specified mRNA sequence. The ribozyme recognizes and then binds eEF2 kinase mRNA through complementary base pairing. Once it is bound to the correct eEF2 kinase mRNA site, the ribozyme acts enzymatically to cut the eEF2 kinase mRNA. Cleavage of the mRNA by a ribozyme destroys its ability to direct synthesis of the corresponding polypeptide. Once the ribozyme has cleaved its eEF2 kinase mRNA sequence, it is released and can repeatedly bind and cleave at other mRNAs.

Ribozyme forms include a hammerhead motif, a hairpin motif, a hepatitis delta virus, group I intron or RNaseP RNA (in association with an RNA guide sequence) motif or Neurospora VS RNA motif. Ribozymes possessing a hammerhead or hairpin structure are readily prepared since these catalytic RNA molecules can be expressed within cells from eukaryotic promoters (Chen, et al. (1992) Nucleic Acids Res. 20:4581-9). A ribozyme of the present invention can be expressed in eukaryotic cells from the appropriate DNA vector. If desired, the activity of the ribozyme may be augmented by its release from the primary transcript by a second ribozyme (Ventura, et al. (1993) Nucleic Acids Res. 21:3249-55).

The term "vectors" relates to plasmids as well as to viral vectors, such as recombinant viruses, or the nucleic acid encoding the recombinant virus.

Ribozymes may be chemically synthesized by combining an oligodeoxyribonucleotide with a ribozyme catalytic domain (20 nucleotides) flanked by sequences that hybridize to the eEF2 kinase mRNA after transcription. The oligodeoxyribonucleotide is amplified by using the substrate binding sequences as primers. The amplification product is cloned into a eukaryotic expression vector.

Ribozymes are expressed from transcription units inserted into DNA, RNA, or viral vectors. Transcription of the ribozyme sequences are driven from a promoter for eukaryotic RNA polymerase I (pol (I), RNA polymerase II (pol II), or RNA polymerase III (pol III). Transcripts from pol II or pol III promoters will be expressed at high levels in all cells; the levels of a given pol II promoter in a given cell type will depend on nearby gene regulatory sequences. Prokaryotic RNA polymerase promoters are also used, providing that the prokaryotic RNA polymerase enzyme is expressed in the appropriate cells (Gao and Huang, (1993) Nucleic Acids Res. 21:2867-72). It has been demonstrated that ribozymes expressed from these promoters can function in mammalian cells (Kashani-Sabet, et al. (1992) Antisense Res. Dev. 2:3-15).

siRNA

A particularly preferred inhibitory agent is a small interfering RNA (siRNA). siRNA, preferably short hairpin RNA (shRNA), mediate the post-transcriptional process of gene silencing by double stranded RNA (dsRNA) that is homologous in sequence to the silenced RNA. siRNA according to the present invention comprises a sense strand of 17-25 nucleotides complementary or homologous to a contiguous 17-25 nucleotide sequence selected from the group of sequences encoding SEQ ID NO: 2, preferably from SEQ ID NO: 1, and an antisense strand of 17-23 nucleotides complementary to the sense strand. The most preferred siRNA comprises sense and anti-sense strands that are 100 percent complementary to each other and the eEF2 kinase polynucleotide sequence. Preferably the siRNA further comprises a loop region linking the sense and the antisense strand. A self-complementing single stranded siRNA molecule polynucleotide according to the present invention comprises a sense portion and an antisense portion connected by a loop region linker. The loop can be any length but is preferably 4-30 nucleotides long. Self-complementary single stranded siRNAs form hairpin loops and are more stable than ordinary dsRNA. In addition, they are more easily produced from vectors.

Analogous to antisense RNA, the siRNA can be modified to confirm resistance to nucleolytic degradation, or to enhance activity, or to enhance cellular distribution, or to enhance cellular uptake, such modifications may consist of modified internucleoside linkages, modified nucleic acid bases, modified sugars and/or chemical linkage the siRNA to one or more moieties or conjugates.

The present invention also relates to compositions, and methods using said compositions, comprising a DNA expression vector capable of expressing a polynucleotide capable of increasing resistance to cell damage and is described hereinabove as an expression inhibition agent.

Intracellular Binding Protein

A special aspect of these compositions and methods relates to the down-regulation or blocking of the expression of a eEF2 kinase by the induced expression of a polynucleotide encoding an intracellular binding protein that is capable of selectively interacting with the eEF2 kinase polypeptide. An intracellular binding protein includes any protein capable of selectively interacting, or binding, with the polypeptide in the cell in which it is expressed and neutralizing the function of the polypeptide. Preferably, the intracellular binding protein is a neutralizing antibody or a fragment of a neutralizing antibody having binding affinity to an epitope of the eEF2 kinase of SEQ ID NO: 2. More preferably, the intracellular binding protein is a single chain antibody.

The term "binding affinity" is a property that describes how strongly two or more compounds associate with each other in a non-covalent relationship. Binding affinities can be characterized qualitatively, (such as "strong", "weak", "high", or "low") or quantitatively (such as measuring the $K_D$).

A special embodiment of this composition comprises the expression-inhibiting agent selected from the group consisting of antisense RNA, antisense oligodeoxynucleotide (ODN), a ribozyme that cleaves the polyribonucleotide coding for SEQ ID NO: 2, and a small interfering RNA (siRNA) that is sufficiently homologous to a portion of the polyribonucleotide coding for SEQ ID NO: 2, such that the siRNA interferes with the translation of the eEF2 kinase polyribonucleotide to the eEF2 kinase polypeptide.

The polynucleotide expressing the expression-inhibiting agent is preferably included within a vector. The polynucleic acid is operably linked to signals enabling expression of the nucleic acid sequence and is introduced into a cell utilizing, preferably, recombinant vector constructs, which will express the antisense nucleic acid once the vector is introduced into the cell. A variety of viral-based systems are available, including adenoviral, retroviral, adeno-associated viral, lentiviral, herpes simplex viral or a sendaviral vector systems, and all may be used to introduce and express polynucleotide sequence for the expression-inhibiting agents in eEF2 kinase-expressing cells.

The term "operably linked" or "operably inserted" means that the regulatory sequences necessary for expression of the coding sequence are placed in a nucleic acid molecule in the appropriate positions relative to the coding sequence so as to enable expression of the coding sequence. This same definition is sometimes applied to the arrangement other transcription control elements (e. g. enhancers) in an expression vector. Transcriptional and translational control sequences are DNA expression regulatory sequences, such as promoters, enhancers, polyadenylation signals, terminators, and the like, that provide for the expression of a coding sequence in a host cell.

The terms "promoter", "promoter region" or "promoter sequence" refer generally to transcriptional regulatory regions of a gene, which may be found at the 5' or 3'side of the coding region, or within the coding region, or within introns. Promoters that may be used in the expression vectors of the present invention include both constitutive promoters and regulated (inducible) promoters.

Typically, a promoter is a DNA regulatory region capable of binding RNA polymerase in a cell and initiating transcription of a downstream (3'direction) coding sequence. The typical 5'promoter sequence is bounded at its 3'terminus by the transcription initiation site and extends upstream (5'direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

In a preferred embodiment, the viral element is derived from an adenovirus. Other embodiments of the present invention use retroviral vector systems which can be constructed from different types of retrovirus, such as, MoMuLV ("murine Moloney leukemia virus" MSV ("murine Moloney sarcoma virus"), HaSV ("Harvey sarcoma virus"); SNV ("spleen necrosis virus"); RSV ("Rous sarcoma virus") and Friend virus. Lentiviral vector systems may also be used in the practice of the present invention. In other embodiments of the present invention, adeno-associated viruses ("AAV") are utilized.

Preferably, the viral vectors used in the methods of the present invention are replication defective. Such replication defective vectors will usually pack at least one region that is necessary for the replication of the virus in the infected cell. These regions can either be eliminated (in whole or in part), or be rendered non-functional by any technique known to a person skilled in the art. These techniques include the total removal, substitution, partial deletion or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome, which are necessary for encapsidating, the viral particles.

In the vector construction, the polynucleotide agents of the present invention may be linked to one or more regulatory regions. Selection of the appropriate regulatory region or regions is a routine matter, within the level of ordinary skill in the art. Regulatory regions include promoters, and may include enhancers, suppressors, etc.

Additional vector systems include the non-viral systems that facilitate introduction of polynucleotide agents into a patient. For example, a DNA vector encoding a desired sequence can be introduced in vivo by lipofection. Synthetic cationic lipids designed to limit the difficulties encountered with liposome-mediated transfection can be used to prepare liposomes for in vivo transfection of a gene encoding a marker (Felgner, et. al. (1987) Proc. Natl. Acad Sci. USA 84:7413-7); see Mackey, et al. (1988) Proc. Natl. Acad. Sci. USA 85:8027-31; Ulmer, et al. (1993) Science 259:1745-8). The use of cationic lipids may promote encapsulation of negatively charged nucleic acids, and also promote fusion with negatively charged cell membranes (Felgner and Ringold, (1989) Nature 337:387-8). Particularly useful lipid compounds and compositions for transfer of nucleic acids are described in International Patent Publications WO 95/18863 and WO 96/17823, and in U.S. Pat. No. 5,459,127. The use of lipofection to introduce exogenous genes into the specific organs in vivo has certain practical advantages and directing transfection to particular cell types would be particularly advantageous in a tissue with cellular heterogeneity, for example, pancreas, liver, kidney, and the brain. Lipids may be chemically coupled to other molecules for the purpose of targeting. Targeted peptides, e.g., hormones or neurotransmitters, and proteins for example, antibodies, or non-peptide molecules could be coupled to liposomes chemically. Other molecules are also useful for facilitating transfection of a nucleic acid in vivo, for example, a cationic oligopeptide (e.g., International Patent Publication WO 95/21931), peptides derived from DNA binding proteins (e.g., International Patent Publication WO 96/25508), or a cationic polymer (e.g., International Patent Publication WO 95/21931).

It is also possible to introduce a DNA vector in vivo as a naked DNA plasmid (see U.S. Pat. Nos. 5,693,622, 5,589,466 and 5,580,859). Naked DNA vectors for therapeutic purposes can be introduced into the desired host cells by methods known in the art, e.g., transfection, electroporation, microinjection, transduction, cell fusion, DEAE dextran, calcium phosphate precipitation, use of a gene gun, or use of a DNA vector transporter (see, e.g., Wilson, et al. (1992) J. Biol. Chem. 267:963-7; Wu and Wu, (1988) J. Biol. Chem. 263:14621-4; Hartmut, et al. Canadian Patent Application No. 2,012,311, filed Mar. 15, 1990; Williams, et al (1991). Proc. Natl. Acad. Sci. USA 88:2726-30). Receptor-mediated DNA delivery approaches can also be used (Curiel, et al. (1992) Hum. Gene Ther. 3:147-54; Wu and Wu, (1987) J. Biol. Chem. 262:4429-32).

Methods of Treatment

In another aspect, the invention relates to a method of treating and/or preventing a disease characterized by an increase in eEF2 kinase activity in a patient by administering to the patient a therapeutically effective amount of a composition comprising a compound that decreases phosphorylation of eEF2 kinase substrate by eEF2 kinase. The term "condition" or "disease" means the overt presentation of symptoms (i.e., illness) or the manifestation of abnormal clinical indicators (e.g., biochemical indicators). Alternatively, the term "disease" refers to a genetic or environmental risk of or propensity for developing such symptoms or abnormal clinical indicators. A variety of disease states may be treated utilizing the methods and compounds of the present invention. In preferred embodiments the disease state is selected from the group consisting of hypoxia, anoxia, ischemia, stroke, and neurogenerative diseases such as Parkinson's or Alzheimer's disease.

In yet another aspect, the invention relates to a method of protecting a cell population in a patient from a potential source of cell damage selected from chemotherapy agents, ionizing radiation, ultraviolet radiation, and free radicals by administering to the patient a therapeutically effective amount of a composition including a compound that decreases phosphorylation of eEF2 kinase substrate by eEF2 kinase. In particular, the invention relates to a method of protecting normal tissues during chemotherapy of cancer cells by administering to the patient a therapeutically effective amount of a composition including a compound that decreases phosphorylation of eEF2 kinase substrate by eEF2 kinase. In one aspect of the invention, the compound includes a polynucleotide having a nucleotide sequence complementary to a nucleotide sequence encoding a polypeptide comprising the amino acid sequence of SEQ ID NO: 2. In another aspect, the ionizing radiation includes gamma radiation.

In another aspect, the present invention relates to a knockout mouse, wherein the knockout mouse comprises a disruption in an eEF2 kinase gene. In a preferred embodiment, the mouse is heterozygous for the disruption in the eEF2 kinase gene. In an especially preferred embodiment, the mouse is homozygous for the disruption in the eEF2 kinase gene. In a preferred embodiment, the disruption occurs in a region of the eEF2 kinase gene which encodes a catalytic domain of the eEF2 kinase polypeptide, preferably the region comprises exon 7 or 8 of the eEF2 kinase gene. In an especially preferred embodiment, the mouse exhibits a phenotype selected from the group consisting of extension of life span and resistance to stress-induced cell damage.

In another aspect, the invention relates to an eEF2 kinase knockout construct, comprising a portion of an eEF2 kinase gene, wherein a portion of the eEF2 kinase gene is replaced by a selectable marker. In a preferred embodiment the selectable marker is a gene which encodes for a polypeptide selected from the group consisting of thymidine kinase, neomycin phosphotransferase and hygromycin B phosphotransferase. In an especially preferred embodiment the portion of the eEF2 kinase gene which is replaced comprises exon 7.

In another aspect, the invention relates to a method of producing a mouse with a targeted disruption in an eEF2 kinase gene. The mouse is obtained by transfecting a population of embryonic stem cells with a knockout construct in which comprising a portion of the eEF2 kinase gene with a portion of the eEF2 kinase gene replaced by a marker; selecting a transfected embryonic stem cell which expresses the marker; introducing the transfected ES cell into an embryo of an ancestor of the mouse allowing the embryo to develop to term to produce a chimeric mouse with the knockout construct in its germline; and breeding the chimeric mammal, to produce a heterozygous mouse with a targeted disruption in the eEF2 kinase gene.

An eEF2 kinase knockout construct is typically prepared by isolating a portion of the genomic or cDNA eEF2 kinase nucleotide sequence (usually encoding at least one exon and one intron), and inserting a marker sequence into the eEF2 kinase sequence. The eEF2 kinase gene or gene fragment to be used in preparing this construct may be obtained in a variety of ways. Generally, the eEF2 kinase DNA molecule will be at least about 1 kilobase (kb) in length, and preferably will be 3-4 kb in length, thereby providing sufficient complementary sequence for recognition with chromosomal DNA (i e., homologous recombination) when the knockout construct is introduced into the genomic DNA of the embryonic stem (ES) cell (discussed below).

A naturally occurring genomic eEF2 kinase fragment or cDNA molecule to be used in preparing the knockout construct can be obtained using methods well known in the art such as those described by Sambrook et al. (Molecular Cloning: A Laboratory Manual, Cold Spring Harbor Laboratory Press, Cold Spring Harbor, N.Y. (1989)). Such methods include, for example, PCR amplification of a particular DNA sequence using oligonucleotide primers, or screening a genomic library prepared from cells or tissues that contain the eEF2 kinase gene with a cDNA probe encoding at least a portion of the same or a highly homologous eEF2 kinase gene in order to obtain at least a portion of the eEF2 kinase genomic sequence. Alternatively, if a cDNA sequence is to be used in a knockout construct, the cDNA may be obtained by screening a cDNA library (preferably one prepared from tissues or that express eEF2 kinase, where the tissues or cells are derived from the same or a similar species of mammal as that to be rendered the knockout mammal) with oligonucleotide probes, homologous cDNA probes, or antibodies (where the library is cloned into an expression vector). If a promoter sequence is to be used in the knockout construct, synthetic DNA probes or primers can be designed for screening a genomic library or for amplification using PCR, respectively.

The eEF2 kinase genomic DNA fragment or eEF2 kinase cDNA molecule prepared for use in the knockout construct must be generated in sufficient quantity for genetic manipulation. Amplification may be conducted by 1) placing the fragment into a suitable vector and transforming bacterial or other cells that can rapidly amplify the vector, 2) by PCR amplification, 3) by synthesis with a DNA synthesizer, or 4) by other suitable methods.

The eEF2 kinase genomic DNA fragment, cDNA molecule, or PCR fragment to be used in making the eEF2 kinase knockout construct can be digested with one or more restriction enzymes selected to cut at a location(s) such that a second DNA molecule encoding a marker gene can be inserted in the proper position within the eEF2 kinase genomic DNA fragment, cDNA molecule, or PCR fragment to be used in the construct. The proper position for marker gene insertion is one that will serve to decrease or prevent transcription and/or expression of the full length endogenous eEF2 kinase gene. This position will depend on various factors such as the available restriction sites in the sequence to be cut, whether an exon sequence or a promoter sequence, or both is (are) to be interrupted, and whether several isoforms of eEF2 kinase exist in the mammal (due to alternative splicing) and only one such isoform is to be disrupted. Preferably, the enzyme(s) selected for cutting the eEF2 kinase genomic DNA, cDNA molecule, or PCR fragment will generate a longer arm and a shorter arm, where the shorter arm is at least about 300 base pairs (bp). In some cases, it will be desirable to actually delete a portion or even all of one or more introns or exons of this native genomic or cDNA molecule. In these cases, the eEF2 kinase genomic DNA, cDNA molecule, or PCR fragment can be cut with appropriate restriction endonucleases such that a fragment of the proper size and proper location can be removed.

The marker gene used in the knockout construct can be any nucleic acid molecule that is detectable and/or assayable after it has been incorporated into the genomic DNA of the ES cell, and ultimately the knockout mammal, however typically it is an antibiotic resistance gene or other gene whose expression or presence in the genome can easily be detected. Preferably, the marker gene encodes a polypeptide that does not naturally occur in the mammal. The marker gene is usually operably linked to its own promoter or to another strong promoter such as the thymidine kinase (TK) promoter or the phosphoglycerol kinase (PGK) promoter from any source that will be active or can easily be activated in the cell into which it is inserted; however, the marker gene need not have its own promoter attached, as it may be transcribed using the promoter of the gene to be knocked out. In addition, the marker gene will normally have a polyA sequence attached to its 3' end; this sequence serves to terminate transcription of the marker gene. Preferred marker genes are any antibiotic resistance gene such as neo (the neomycin resistance gene) and beta-gal (beta-galactosidase).

After the eEF2 kinase genomic DNA fragment, cDNA molecule, or PCR fragment has been digested with the appropriate restriction enzyme(s), the marker gene molecule can be ligated with the native genomic DNA or cDNA molecule using methods well known to the skilled artisan and described in Sambrook et al., supra. In some cases, it will be preferable to insert the marker sequence in the reverse or antisense orientation with respect to the eEF2 kinase nucleic acid sequence; this reverse insertion is preferred where the marker gene is operably linked to a particularly strong promoter.

The ends of the DNA molecules to be ligated must be compatible; this can be achieved by either cutting all fragments with those enzymes that generate compatible ends, or by blunting the ends prior to ligation. Blunting can be done using methods well known in the art, such as for example by the use of Klenow fragment (DNA polymerase I) to fill in sticky ends. After ligation, the ligated constructs can be screened by selective restriction endonuclease digestion to determine which constructs contain the marker sequence in the desired orientation.

The ligated DNA knockout construct may be transfected directly into embryonic stem cells (discussed below), or it may first be placed into a suitable vector for amplification prior to insertion. Preferred vectors are those that are rapidly amplified in bacterial cells such as the pBluescript II SK vector (Stratagene, San Diego, Calif.) or pGEM7 (Promega Corp., Madison, Wis.).

The eEF2 kinase knockout construct is typically transfected into stem cells derived from an embryo (embryonic stem cells, or "ES cells"). ES cells are undifferentiated cells that are capable of taking up extra-chromosomal DNA and incorporating it into their chromosomal DNA. Generally, the ES cells used to produce the knockout mammal will be of the same species as the knockout mammal to be generated. Thus for example, mouse embryonic stem cells will usually be used for generation of knockout mice.

The embryonic stem cell line used is typically selected for its ability to integrate into and become part of the germ line of a developing embryo so as to create germ line transmission of the knockout construct. Thus, any ES cell line that is believed to have this capability is suitable for use herein. Preferred ES cell lines for generating knockout mice are murine cell lines D3 and E14 (American Type Culture Collection, 12301 Parklawn Drive, Rockville, Md. 20852-1776 USA, catalog nos. CRL 1934 and CRL 1821, respectively), or RW4 (Genome Systems, Inc., 8620 Pennell Drive, St. Louis, Mich. 63114 USA, catalog No. ESVJ-1182). The cells are cultured and prepared for DNA insertion using methods well known to the skilled artisan such as those set forth by Robertson (in: Teratocarcinomas and Embryonic Stem Cells: A Practical Approach, E. J. Robertson, ed. IRL Press, Washington, D.C. (1987)), by Bradley et al. (Current Topics in Devel. Biol., 20:357-371 (1986)) and by Hogan et al. (Manipulating the Mouse Embryo: A Laboratory Manual, Cold Spring Harbor Laboratory Press, Cold Spring Harbor, N.Y. (1986)).

Insertion (also termed "transfection") of the knockout construct into the ES cells can be accomplished using a variety of methods well known in the art including for example, electroporation, microinjection, and calcium phosphate treatment (see Lovell-Badge, in Robertson, ed., supra). A preferred method of insertion is electroporation.

The eEF2 kinase knockout construct DNA molecules to be transfected into the cells can first be linearized if the knockout construct has previously been inserted into a circular vector. Linearization can be accomplished by digesting the DNA with a suitable restriction endonuclease selected to cut only within the vector sequence and not within the knockout construct sequence.

The isolated eEF2 kinase knockout construct DNA can be added to the ES cells under appropriate conditions for the insertion method chosen. Where more than one construct is to be introduced into the ES cells, the DNA molecules encoding each construct can be introduced simultaneously or sequentially. Optionally, homozygous eEF2 kinase knockout ES cells may be generated by adding excessive eEF2 kinase knockout construct DNA to the cells, or by conducting successive rounds of transfection in an attempt to achieve homologous recombination of the knockout construct on both endogenous eEF2 kinase alleles.

If the ES cells are to be electroporated, the ES cells and knockout construct DNA are exposed to an electric pulse using an electroporation machine and following the manufacturer's guidelines for use. After electroporation, the cells are typically allowed to recover under suitable incubation conditions. The cells are then screened for the presence of the knockout construct.

Screening the ES cells can be accomplished using a variety of methods, but typically, one screens for the presence of the marker sequence portion of the knockout construct. Where the marker gene is an antibiotic resistance gene, the cells can be cultured in the presence of an otherwise lethal concentration of antibiotic. Those cells that survive have presumably integrated the knockout construct. If the marker gene is other than an antibiotic resistance gene, a Southern blot of the ES cell genomic DNA can be probed with a sequence of DNA designed to hybridize only to the marker sequence. If the marker gene is a gene that encodes an enzyme whose activity can be detected (e.g., beta-galactosidase), the enzyme substrate can be added to the cells under suitable conditions, and the enzymatic activity of the marker gene can be analyzed.

The knockout construct may integrate into several locations in the ES cell genome, and may integrate into a different location in each cell's genome, due to the occurrence of random insertion events; the desired location of insertion is within the eEF2 kinase endogenous gene sequence. Typically, less than about 1-10 percent of the ES cells that take up the knockout construct will actually integrate the knockout construct in the desired location. To identify those cells with proper integration of the knockout construct, chromosomal DNA can be extracted from the cells using standard methods such as those described by Sambrook et al., supra. This DNA can then be probed on a Southern blot with a probe or probes designed to hybridize to the knockout construct DNA digested with (a) particular restriction enzyme(s). Alternatively, or additionally, a specific genomic DNA sequence can be amplified by PCR with probes specifically designed to amplify that DNA sequence such that only those cells containing the knockout construct in the proper position will generate DNA fragments of the proper size.

Accordingly, the present invention also relates to an isolated cell, wherein the cell contains a disruption in the eEF2 kinase gene. The cell can be any type of cell, including cells isolated from a non-human animal that is homozygous or heterozygous for the disruption to the gene, for example, mouse embryo fibroblasts (MEFs). In preferred embodiments the cell is an undifferentiated cell. In particularly preferred embodiments the undifferentiated cell is selected from the group consisting of a stem cell, an embryonic stem cell, an oocyte and an embryonic cell. In especially preferred embodiment, the cell comprises a disruption of the eEF2 kinase gene which encodes a catalytic domain of the eEF2 kinase polypeptide. In an especially preferred embodiment, the disruption comprises a portion of an eEF2 kinase gene, wherein a portion of the eEF2 kinase gene is replaced by a selectable marker. In a preferred embodiment the selectable marker is a gene which encodes for a polypeptide selected from the group consisting of thymidine kinase, neomycin phosphotransferase and hygromycin B phosphotransferase. In an especially preferred embodiment the portion of the eEF2 kinase gene which is replaced comprises exon 7.

After suitable ES cells containing the knockout construct in the proper location have been identified, the cells can be incorporated into an embryo. Incorporation may be accomplished in a variety of ways. A preferred method of incorporation of ES cells is by microinjection into an embryo that is at the blastocyst stage of development. For microinjection, about 10-30 cells are collected into a micropipet and injected into a blastocyst to integrate the ES cell into the developing blastocyst.

The suitable stage of development for the blastocyst is species dependent, however for mice it is about 3.5 days. The blastocysts can be obtained by perfusing the uterus of pregnant females. Suitable methods for accomplishing this are known to the skilled artisan, and are set forth for example by Bradley (in Robertson, ed., supra).

While any blastocyst of the right age/stage of development is suitable for use, preferred blastocysts are male and have genes coding for a coat color or other phenotypic marker that is different from the coat color or other phenotypic marker encoded by the ES cell genes. In this way, the offspring can be screened easily for the presence of the knockout construct by looking for mosaic coat color or other phenotypic marker (indicating that the ES cell is incorporated into the developing embryo). Thus, for example, if the ES cell line carries the genes for white fur, the embryo selected will preferably carry genes for black or brown fur.

An alternate method of preparing an embryo containing ES cells that possess the knockout construct is to generate "aggregation chimeras". A morula of the proper developmental stage (about 2 1/2 days old for mice) is isolated. The zona pellucida can be removed by treating the morula with a solution of mild acid for about 30 seconds, thereby exposing the "clump" of cells that comprise the morula. Certain types of ES cells such as the Ri cell line for mice can then be co-cultured with the morula cells, forming an aggregation chimera embryo of morula and ES cells.

A refinement of the aggregation chimera embryo method can be used to generate an embryo comprised of essentially only those ES cells containing the knockout construct. In this technique, a very early stage zygote (e.g., a two-cell stage zygote for mice) is given a mild electric shock. This shock serves to fuse the nuclei of the cells in the zygote thereby generating a single nucleus that has two-fold (or more) the DNA of a naturally occurring zygote of the same developmental stage. These zygotic cells are excluded from the developing embryo proper, and contribute only to forming accessory embryonic structures such as the extra-embryonic membrane. Therefore, when ES cells are co-cultured with the zygotic cells, the developing embryo is comprised exclusively of ES cells.

After the ES cells have been incorporated, the aggregation chimera or transfected embryo can be implanted into the uterus of a pseudopregnant foster mother. While any foster mother may be used, preferred foster mothers are typically selected for their ability to breed and reproduce well, and for their ability to care for their young. Such foster mothers are typically prepared by mating with vasectomized males of the same species. The pseudopregnant stage of the foster mother is important for successful implantation, and it is species dependent. For mice, this stage is about 2-3 days pseudopregnant.

Offspring that are born to the foster mother may be screened initially for mosaic coat color or other phenotype marker where the phenotype selection strategy (such as coat color, as described above) has been employed. In addition, or as an alternative, chromosomal DNA obtained from tail tissue of the offspring may be screened for the presence of the knockout construct using Southern blots and/or PCR as described above. The offspring that are positive for the eEF2 kinase knockout construct will typically be heterozygous, although some homozygous knockouts may exist, and can typically be detected by visually quantifying the amount of probe that hybridizes to the Southern blots.

If homozygous knockout mammals are desired, they can be prepared by crossing those heterozygous offspring believed to carry the knockout construct in their germ line to each other; such crosses may generate homozygous knockout animals. If it is unclear whether the offspring will have germ line transmission, they can be crossed with a parental or other strain and the offspring screened for heterozygosity. Homozygotes may be identified by Southern blotting of equivalent amounts of genomic DNA from mammals that are the product of this cross, as well as mammals of the same species that are known heterozygotes, and wild-type mammals. Probes to screen the Southern blots for the presence of the knockout construct in the genomic DNA can be designed as set forth above.

Other means of identifying and characterizing the knockout offspring are also available. For example, Northern blots can be used to probe mRNA obtained from various tissues of the offspring for the presence or absence of transcripts encoding either the gene knocked out, the marker gene, or both. In addition, Western blots can be used to assess the level of expression of the gene knocked out in various tissues of these offspring by probing the Western blot with an antibody against the protein encoded by the gene knocked out, or an antibody against the marker gene product, where this gene is expressed. Finally, in situ analysis (such as fixing the cells and labeling with antibody) and/or FACS (fluorescence activated cell sorting) analysis of various cells from the offspring can be conducted using suitable antibodies to look for the presence or absence of the knockout construct gene product.

Both the heterozygous and homozygous eEF2 kinase knockout mammals of this invention will have a variety of uses, since eEF2 kinase has been implicated in regulation increased life span and increased resistance to cell damage.

A functional knockout may also be achieved by the introduction of an anti-sense construct that blocks expression of eEF2 kinase.

Compositions

The present invention also provides biologically compatible, cell damage-inhibiting compositions comprising an effective amount of one or more compounds identified as eEF2 kinase inhibitors, and/or the expression-inhibiting agents as described hereinabove. In certain aspects, the invention relates to a pharmaceutical composition for the treatment or prevention of a condition involving cell damage or a susceptibility to cell damage, comprising a therapeutically effective amount of a compound that decreases phosphorylation of eEF2 by eEF2 kinase. In another aspect, the compound includes a polynucleotide comprising a nucleotide sequence complementary to a nucleotide sequence encoding a polypeptide comprising the amino acid sequence of SEQ ID NO: 2.

The term "effective amount" or "therapeutically effective amount" means that amount of a compound or agent that will elicit the biological or medical response of a subject that is being sought by a medical doctor or other clinician.

A biologically compatible composition is a composition, that may be solid, liquid, gel, or other form, in which the compound, polynucleotide, vector, and antibody of the invention is maintained in an active form, e.g., in a form able to effect a biological activity. For example, a compound of the invention would have inverse agonist or antagonist activity on the eEF2 kinase; a nucleic acid would be able to replicate, translate a message, or hybridize to a complementary mRNA of a eEF2 kinase; a vector would be able to transfect a eEF2 kinase cell and expression the antisense, antibody, ribozyme or siRNA as described hereinabove; an antibody would bind a eEF2 kinase polypeptide domain.

A preferred biologically compatible composition is an aqueous solution that is buffered using, e.g., Tris, phosphate, or HEPES buffer, containing salt ions. Usually the concentration of salt ions will be similar to physiological levels. Biologically compatible solutions may include stabilizing agents and preservatives. In a more preferred embodiment, the biocompatible composition is a pharmaceutically acceptable composition. Such compositions can be formulated for administration by topical, oral, parenteral, intranasal, subcutaneous, and intraocular, routes. Parenteral administration is meant to include intravenous injection, intramuscular injection, intraarterial injection or infusion techniques. The composition may be administered parenterally in dosage unit formulations containing standard, well-known non-toxic physiologically acceptable carriers, adjuvants and vehicles as desired.

The term "carrier" means a non-toxic material used in the formulation of pharmaceutical compositions to provide a medium, bulk and/or useable form to a pharmaceutical composition. A carrier may comprise one or more of such materials such as an excipient, stabilizer, or an aqueous pH buffered solution. Examples of physiologically acceptable carriers include aqueous or solid buffer ingredients including phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

A particularly preferred embodiment of the present composition invention is a cell damage-inhibiting pharmaceutical composition comprising a therapeutically effective amount of an expression-inhibiting agent as described hereinabove, in admixture with a pharmaceutically acceptable carrier.

Another preferred embodiment is a pharmaceutical composition for the treatment or prevention of a condition related to cell damage, or a susceptibility to the condition, comprising an effective cell damage-inhibiting amount of a eEF2 kinase antagonist or inverse agonist, its pharmaceutically acceptable salts, hydrates, solvates, or prodrugs thereof in admixture with a pharmaceutically acceptable carrier.

The term "pharmaceutically acceptable salts" refers to the non-toxic, inorganic and organic acid addition salts, and base addition salts, of compounds of the present invention. These salts can be prepared in situ during the final isolation and purification of compounds useful in the present invention.

The term "solvate" means a physical association of a compound useful in this invention with one or more solvent molecules. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient. Pharmaceutical compositions for oral use can be prepared by combining active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethyl-cellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate. Dragee cores may be used in conjunction with suitable coatings, such as concentrated sugar solutions, which may also contain gum arabic, talc, polyvinyl-pyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations that can be used orally include push-fit capsules made of gelatin, as well as soft, sealed capsules made of gelatin and a coating, such as glycerol or sorbitol. Push-fit capsules can contain active ingredients mixed with filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Preferred sterile injectable preparations can be a solution or suspension in a non-toxic parenterally acceptable solvent or diluent. Examples of pharmaceutically acceptable carriers are saline, buffered saline, isotonic saline (e.g. monosodium or disodium phosphate, sodium, potassium; calcium or magnesium chloride, or mixtures of such salts), Ringer's solution, dextrose, water, sterile water, glycerol, ethanol, and combinations thereof 1,3-butanediol and sterile fixed oils are conveniently employed as solvents or suspending media. Any bland fixed oil can be employed including synthetic mono- or di-glycerides. Fatty acids such as oleic acid also find use in the preparation of injectables.

The composition medium can also be a hydrogel, which is prepared from any biocompatible or non-cytotoxic homo- or hetero-polymer, such as a hydrophilic polyacrylic acid polymer that can act as a drug absorbing sponge. Certain of them, such as, in particular, those obtained from ethylene and/or propylene oxide are commercially available. A hydrogel can be deposited directly onto the surface of the tissue to be treated, for example during surgical intervention.

Embodiments of pharmaceutical compositions of the present invention comprise a replication defective recombinant viral vector encoding the polynucleotide inhibitory agent of the present invention and a transfection enhancer, such as poloxamer. An example of a poloxamer is Poloxamer 407, which is commercially available (BASF, Parsippany, N.J.) and is a non-toxic, biocompatible polyol. A poloxamer impregnated with recombinant viruses may be deposited directly on the surface of the tissue to be treated, for example during a surgical intervention. Poloxamer possesses essentially the same advantages as hydrogel while having a lower viscosity.

The active expression-inhibiting agents may also be entrapped in microcapsules prepared, for example, by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (1980) 16th edition, Osol, A. Ed.

Sustained-release preparations may be prepared. Suitable examples of sustained-release preparations include semi-permeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™. (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

As defined above, therapeutically effective dose means that amount of protein, polynucleotide, peptide, or its antibodies, agonists or antagonists, which ameliorate the symptoms or condition. Therapeutic efficacy and toxicity of such compounds can be determined by standard pharmaceutical procedures in cell cultures or experimental animals, e.g., ED50

(the dose therapeutically effective in 50% of the population) and LD50 (the dose lethal to 50% of the population). The dose ratio of toxic to therapeutic effects is the therapeutic index, and it can be expressed as the ratio, LD50/ED50. Pharmaceutical compositions that exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

For any compound, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. The exact dosage is chosen by the individual physician in view of the patient to be treated. Dosage and administration are adjusted to provide sufficient levels of the active moiety or to maintain the desired effect. Additional factors which may be taken into account include the severity of the disease state, age, weight and gender of the patient; diet, desired duration of treatment, method of administration, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

The pharmaceutical compositions according to this invention may be administered to a subject by a variety of methods. They may be added directly to tissues, complexed with cationic lipids, packaged within liposomes, or delivered to eEF2 kinase-expressing cells by other methods known in the art. Localized administration to the desired tissues may be done by direct injection, transdermal absorption, catheter, infusion pump or stent. The DNA, DNA/vehicle complexes, or the recombinant virus particles are locally administered to the site of treatment. Alternative routes of delivery include, but are not limited to, intravenous injection, intramuscular injection, subcutaneous injection, aerosol inhalation, oral (tablet or pill form), topical, systemic, ocular, intraperitoneal and/or intrathecal delivery. Examples of ribozyme delivery and administration are provided in Sullivan et al. WO 94/02595.

Antibodies according to the invention may be delivered as a bolus only, infused over time or both administered as a bolus and infused over time. Those skilled in the art may employ different formulations for polynucleotides than for proteins. Similarly, delivery of polynucleotides or polypeptides will be specific to particular cells, conditions, locations, etc.

As discussed hereinabove, recombinant viruses may be used to introduce DNA encoding polynucleotide agents useful in the present invention. Recombinant viruses according to the invention are generally formulated and administered in the form of doses of between about $10^4$ and about $10^{14}$ pfu. In the case of AAVs and adenoviruses, doses of from about $10^6$ to about $10^{11}$ pfu are preferably used. The term pfu ("plaque-forming unit") corresponds to the infective power of a suspension of virions and is determined by infecting an appropriate cell culture and measuring the number of plaques formed. The techniques for determining the pfu titre of a viral solution are well documented in the prior art.

The polypeptides or the polynucleotides employed in the methods of the present invention may be free in solution, affixed to a solid support, borne on a cell surface, or located intracellularly. To perform the methods it is feasible to immobilize either the polypeptide of the present invention or the compound to facilitate separation of complexes from uncomplexed forms of the polypeptide, as well as to accommodate automation of the assay. Interaction (e.g., binding of) of the polypeptide of the present invention with a compound can be accomplished in any vessel suitable for containing the reactants. Examples of such vessels include microtitre plates, test tubes, and microcentrifuge tubes. In one embodiment, a fusion protein can be provided which adds a domain that allows the polypeptide to be bound to a matrix. For example, the polypeptide of the present invention can be "His" tagged, and subsequently adsorbed onto Ni-NTA microtitre plates, or ProtA fusions with the polypeptides of the present invention can be adsorbed to IgG, which are then combined with the cell lysates (e.g., ($^{35}$S-labelled) and the candidate compound, and the mixture incubated under conditions favorable for complex formation (e.g., at physiological conditions for salt and pH). Following incubation, the plates are washed to remove any unbound label, and the matrix is immobilized. The amount of radioactivity can be determined directly, or in the supernatant after dissociation of the complexes. Alternatively, the complexes can be dissociated from the matrix, separated by SDS-PAGE, and the level of the protein binding to the protein of the present invention quantitated from the gel using standard electrophoretic techniques.

Other techniques for immobilizing protein on matrices can also be used in the method of identifying compounds. For example, either the polypeptide of the present invention or the compound can be immobilized utilizing conjugation of biotin and streptavidin. Biotinylated protein molecules of the present invention can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the polypeptides of the present invention but which do not interfere with binding of the polypeptide to the compound can be derivatized to the wells of the plate, and the polypeptide of the present invention can be trapped in the wells by antibody conjugation. As described above, preparations of a labeled candidate compound are incubated in the wells of the plate presenting the polypeptide of the present invention, and the amount of complex trapped in the well can be quantitated.

EXAMPLES

Using a mouse knockout model system, it has been determined that loss of eEF2 kinase activity increases protein synthesis and degradation rates and reduces damage to a cell or increases resistance to damage to a cell. Mice lacking a functional eEF2 kinase appear and have normal development, behavior and reproduction.

Example 1

Plasmids, Antibodies and Cells

Retroviral vector used for eEF2 kinase overexpression is constructed by subcloning of eEF2 kinase cDNA from the pSIT retroviral vector[7] into LXSN vector (Clontech) using Eco RI/XhoI cloning sites. Stable cell line is prepared through infection of MEFs with pBabe-neo retroviral vector containing SV-40 large T antigen (a kind gift from Dr. J. Yuan). GSE 56 cell lines are established using retroviral vector LXSP, containing GSE56[12]. LXSP vector is prepared from LXSN vector by the substitution of neomycin marker with puromycin. Antibodies against p21 (F5) and p53 (Ab-1) are from Calbiochem Inc.; antibodies against eEF2 and phospho-eEF2 are from Cell Signaling Inc. eEF2 kinase$^{-/-}$ and eEF2 kinase$^{+/+}$ primary mouse embryonic fibroblasts used in this study are isolated from 10-12 day embryos following standard protocols. Unless indicated, all cell lines are maintained in DMEM with 10% fetal bovine serum.

Example 2

Transfection and Retroviral Infection

Packaging cells (Phoenix line) are plated in 60-mm plates and transfected with 5 μg of retroviral vector DNA using the standard calcium phosphate procedure. Medium is changed after 8 hours. Virus-containing medium supplemented with 8 μg of Polybrene (Sigma) is collected at 24 and 48 hours post-transfection and used for infection. Infected cells are selected for the resistance to an appropriate selection agent.

Example 3

Western Analysis

For protein expression analysis, cells are washed twice with ice-cold PBS, resuspended in lysis buffer (20 mM Na-phosphate [pH 7.5], 25 mM NaF, 1 mM orthovanadate, 5 mM EDTA), dissolved in Laemmli SDS sample buffer and boiled for 10 minutes. Samples are separated on 5-20% gradient SDS-PAGE and proteins are transferred onto a PVDF membrane. Membranes are incubated with antibodies and developed using ECL Plus reagents (Amersham Biosciences).

Example 4

Drugs and Reagents

Cells are exposed to different drugs and reagents: ionomycin, hydrogen peroxide, doxorubicin and camptothecin (Sigma Inc.) at indicated concentrations and time intervals. Low pH effects are tested using DMEM medium buffered to pH 7, pH 6, pH 5 and pH 4 by 15 mM citric acid and 15 mM sodium phosphate. PFTα is from Calbiochem Inc.

Example 5

Drug Sensitivity Assays

MTT Survival Assay: MEFs used in this study (2×10$^3$ cells per well of a 96 well plate) are incubated in the presence of indicated drugs for 24 hours. Cell viability is determined using the standard MTT assay[30]. Each experiment is repeated three times for each drug and each cell line using three parallel wells for each drug concentration. For colony formation assay cells are treated with indicated drugs for 24 hours and replated with complete DMEM at low density (500 cells per well in 6-well plate) in duplicate. After 10 days colonies are stained with 10 mg/ml methylene blue (Sigma Inc.) in 50% methanol.

Example 6

DNA Ladders, Annexin V Staining and Flow Cytometry

DNA fragmentation pattern (DNA laddering): DNA is analyzed by agarose gel electrophoresis. Cells are incubated in a serum-free media for 48 hours, scraped and centrifuged at 1200 rpm for 10 min. The cell pellets are resuspended in 1 ml of lysis buffer (10 mM Tris-HCl, pH 7.4, 10 mM NaCl, 10 mM EDTA, 100 μg/ml proteinase K) and incubated for 2 hours at 50° C. DNA is extracted with equal volume of phenol-chloroform-isoamyl alcohol. The aqueous phase is precipitated with 2.5 volumes of ice-cold ethanol and 10% volume of 3 M sodium acetate, pH5.2 at −20° C. overnight and analyzed by agarose gel electrophoresis. Flow cytometry performed using annexin V staining: cells are incubated with 600 ng/ml of doxorubicin for 24 hours, then harvested by trypsin digestion, washed with PBS and stained for annexin V assay according to manufacturer's instructions (BD Biosciences, CA). The fluorescence is analyzed by flow cytometry instrument (FASC Scan Cytomics FC500, Beckman Coulter Inc.) and CXP software.

Example 7 eEF2 Kinase Knockout Mouse

Figure 1:
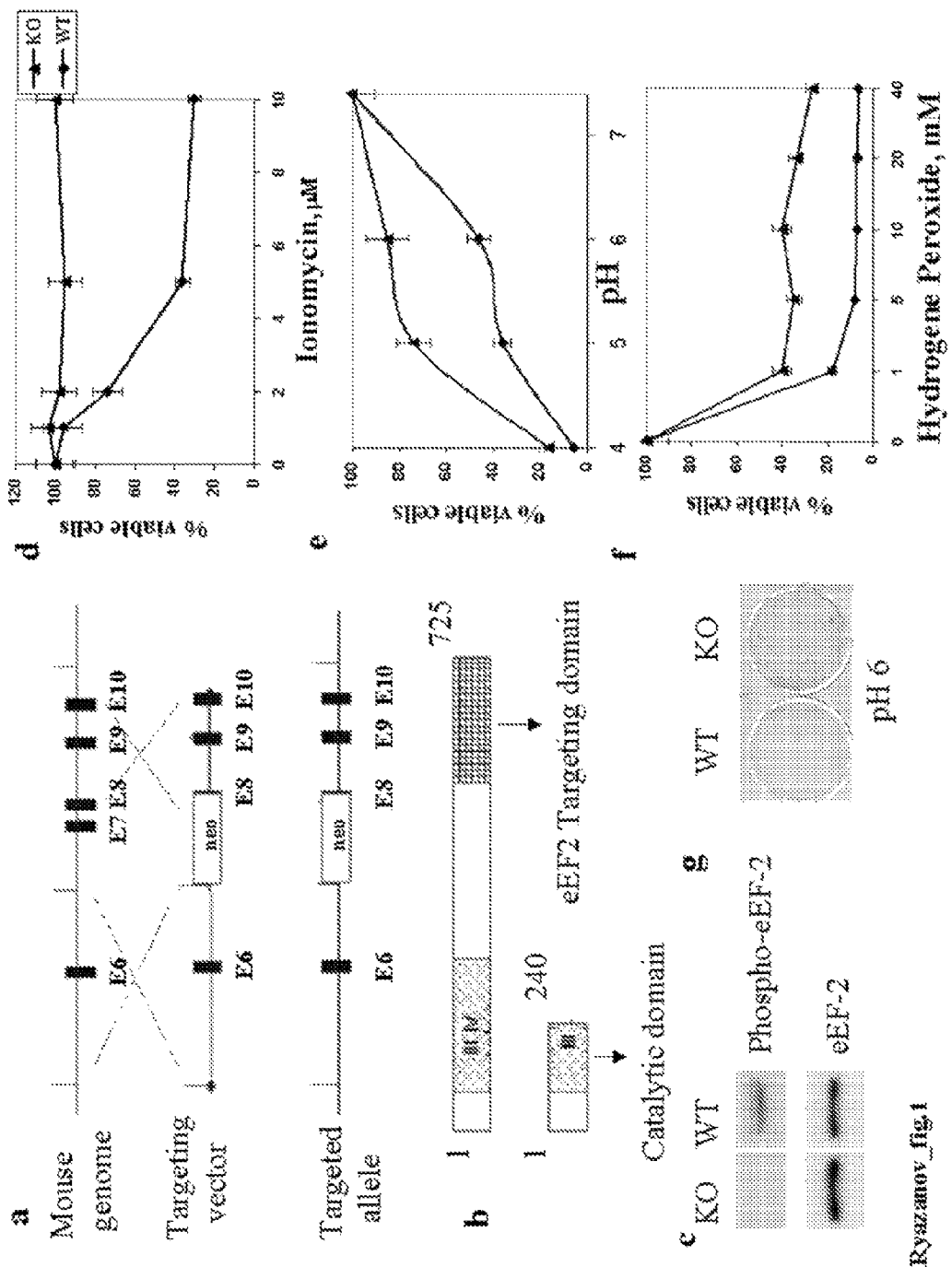
FIG. 1. Ionomycin, acidic pH and hydrogen peroxide cytotoxicity is reduced in eEF2 kinase deficient cells. a. Map of the wild type eEF2K locus, the targeting vector and the mutant eEF2K locus after homologous recombination. b. Schematic representation of wild type eEF2K and predicted truncated eEF2K gene in eEF2K−/− mice. c. Western blot analysis of eEF2 phosphorylation in liver extracts from eEF2K+/+ and eEF2K−/− mice. d. MTT viability assay for eEF2K+/+ (WT) and eEF2K−/− (KO) MEFs after treatment with ionomycin at indicated concentrations for 24 hours. e. Graphs of MTT assay for eEF2K+/+ and eEF2K−/− MEFs incubated at indicated pH for 3 hours. f. Graphs of MTT assay for eEF2K+/+ and eEF2K−/− MEFs incubated with H2O2 at indicated concentrations for 12 hours. g. Colony formation assay of eEF2K+/+ and eEF2K−/− stable cell lines after incubation at pH6 for 24 h.
Figure 2:
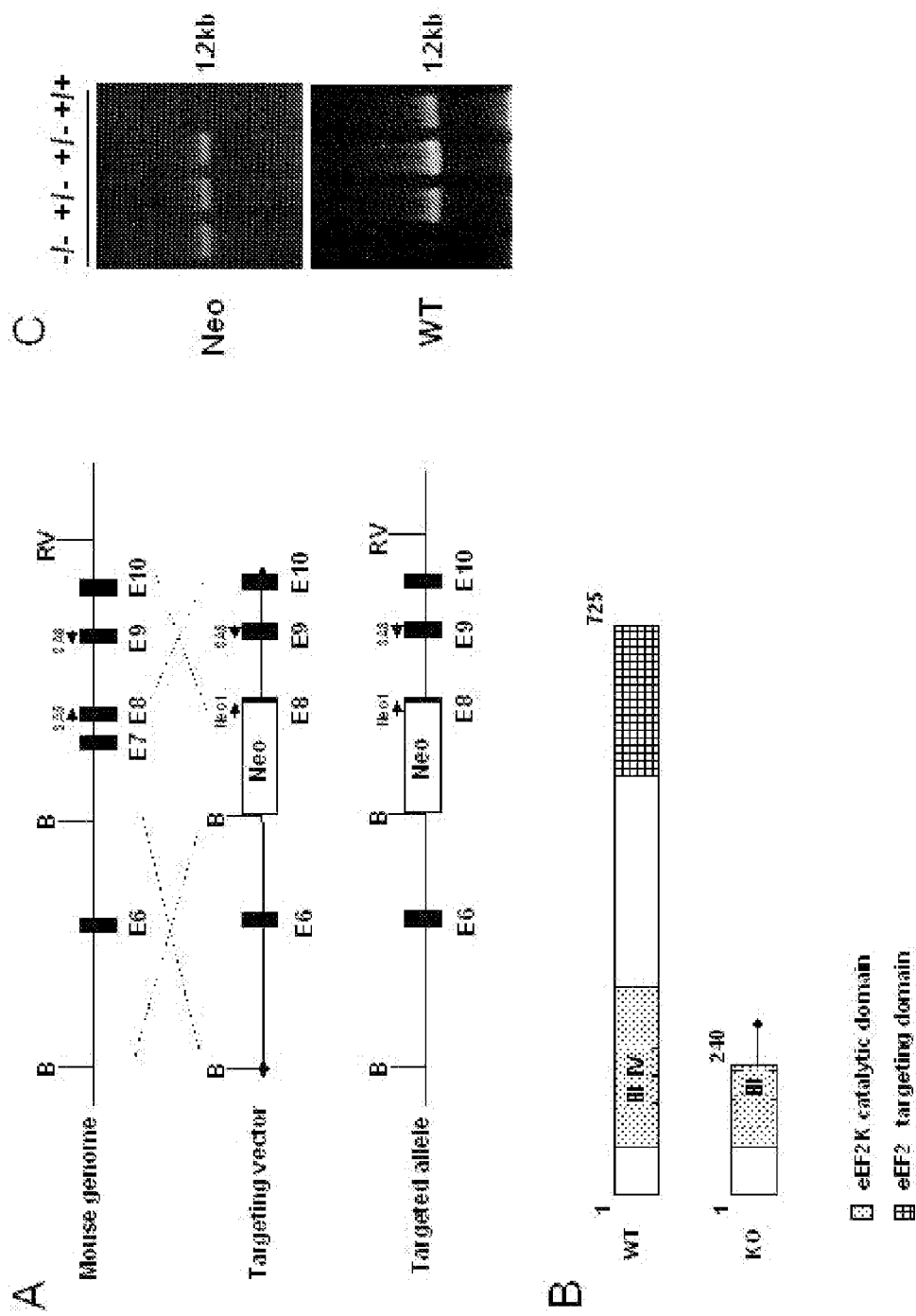
FIG. 2. Generation of eEF2 kinase knockout in mice. (A) The eEF2 gene knockout mice are generated by genomic targeting to the germline transmission. In the eEF2 kinase gene knockout construction, by the homologous recombination, the exon 7 and the majority of exon 8 is replaced by Neo gene cassette that disrupted the catalytic domain of eEF2 kinase. (B) This strategy resulted in truncation of eEF2 kinase and elimination of subdomains IV-IX from its catalytic domain (see Drennan and Ryazanov (2004) Progress in Biophys & Mol. Biol. 85: 1-32 for designation of domains). The correctly targeted ES cell lines are microinjected into C57BL/6J and BaLA/cj host blastocysts. The chimeric mice are generated and they give germline transmission of the disrupted eEF2 gene. (C) The genotypes of mice are inspected by PCR reactions using primer pairs SA8/Neo1 to identify knockout allele and primer pairs SA8/SA5 to detect WT allele (Neo1.

In order to investigate the function of eEF2 kinase an eEF2 kinase knockout mouse is generated by disrupting the eEF2 kinase gene in mouse embryonic stem (ES) cells. A targeting vector is used, in which exon 7 and the majority of exon 8 are replaced with the neomycin resistance gene (FIG. 1a), resulting in the elimination of a portion of the catalytic domain of eEF2 kinase (FIG. 1a, b; FIG. 2A, 2B). eEF2 kinase$^{+/-}$ ES cell clones are identified and used to obtain chimeras and subsequently eEF2k$^{+/-}$ mice. Mating of eEF2 kinase$^{+/-}$ mice produced progeny of eEF2 kinase$^{+/-}$, eEF2 kinase$^{+/+}$ and eEF2 kinase$^{-/-}$ mice with the expected ratio of 2:1:1. No phosphorylated eEF2 is observed in the tissue extracts of the eEF2 kinase$^{-/-}$ mice, indicating their complete lack of eEF2 kinase activity (FIG. 1c). The knockout mice are viable, do not have visible abnormalities and give normal progeny for many generations.

eEF2 kinase is a Ca$^{2+}$/calmodulin-dependent enzyme whose cellular activity is previously demonstrated to increase upon incubation with Ca$^{2+}$ ionophores ionomycin or A23187, which can induce apoptotic cell death. The possible correlation between activation of eEF2 kinase and the resultant phosphorylation of eEF2 and Ca$^{2+}$ ionophore-induced cell death is addressed by comparing the viability of wild type and eEF2 kinase knockout mouse embryonic fibroblasts (MEFs) after incubation of each with different concentrations of ionomycin. As shown in FIG. 1d, exposure of eEF2 kinase$^{+/+}$ MEFs to increasing concentrations of ionomycin from 1 to 10 μM resulted in a progressive decrease of cell viability. Notably, approximately 70% of cells die after incubation for 24 h with 10 μM ionomycin, whereas the same concentrations of ionomycin have virtually no effect on the viability of eEF2 kinase$^{-/-}$ MEFs. These results suggest that activation of eEF2 kinase may facilitate cell death induced by ionomycin and that inactivation of eEF2 kinase results in an increased resistance to damage caused by Ca$^{2+}$ ionophores.

eEF2 kinase can also be activated by acidic pH. Acidic pH is cytotoxic and therefore activation of eEF2 kinase by acidic pH can be involved in the regulation of cell death. The effect of acidic pH on the viability of eEF2 kinase knockout and wild types MEFs is also analyzed. FIG. 1e shows that eEF2 kinase$^{-/-}$ MEFs are significantly more resistant than wild type MEFs to the cytotoxic effect of acidic pH. The increased viability of eEF2 kinase knockout cells in an acidic environment is also observed in the stable cell lines derived from MEFs. Using a low-density clonogenic assay it is shown that after incubation at pH 6 for 3 hours, eEF2 kinase knockout cells produce significantly more colonies than wild type cells (FIG. 1g). eEF2 kinase$^{-/-}$ MEFs are also significantly more resistant than wild type MEFs to hydrogen peroxide (FIG. 1f). Thus, these results demonstrate that knockout of eEF2 kinase increases resistance of cells to stress, induced by $Ca^{2+}$ ionophore and acidic pH, as well as to oxidative stress induced by hydrogen peroxide.

Example 8

Sensitivity to Chemotherapeutic Drugs

Next the sensitivity of knockout and wild type MEFs to the chemotherapeutic drugs camptothecin (CPT) and doxorubicin (DOX) is analyzed. As shown in FIGS. 3a and 3b, eEF2 kinase$^{-/-}$ MEFs and their stable cell lines are significantly more resistant than their wild type counterparts to CPT and DOX, respectively. Introduction of eEF2 kinase cDNA into eEF2 kinase knockout cells restored sensitivity of these cells to DOX to the level observed in wild type cells (FIG. 3c).

To investigate the mode of cell death that is affected by eEF2 an annexin V assay and DNA fragmentation analysis is performed. As shown in FIG. 3d the percentage of apoptotic annexin V positive cells after 24 hours of treatment with doxorubicin is significantly lower in eEF2 kinase$^{-/-}$ cells than in eEF2 kinase$^{+/+}$ cells. Apoptotic DNA ladder formation in wild type and eEF2 kinase knockout cells in response to serum starvation is also analyzed. Incubation of eEF2 kinase$^{+/+}$ cells in serum free media for 48 h resulted in significant DNA fragmentation, whereas no DNA ladder formation is observed in eEF2 kinase$^{-/-}$ cells incubated under the same conditions (FIG. 3e). This suggests that the absence of eEF2 kinase results in inhibition of apoptosis and therefore eEF2 kinase might be a factor that facilitates apoptosis.

Since the tumor suppressor p53 is known to be involved in modulating the sensitivity of MEFs to various cytotoxic drugs and induction of apoptosis, it is determined whether the effects of the eEF2 kinase knockout on cell sensitivity to doxorubicin might depend on functional p53. Sensitivity to DOX is assessed in wild type and eEF2 kinase knockout MEFs in which p53 is inactivated by overexpression of GSE 56, a carboxyl-terminal portion of p53 that acts as a dominant negative p53 mutant, or by incubation with pifithrin α (PFT α), a chemical p53 inhibitor. Inactivation of p53 either by GSE56 or PFTα only slightly affected drug sensitivity of eEF2 kinase knockout fibroblasts, while strongly decreasing sensitivity of wild type cells (FIG. 4a, b), suggesting that the effect of eEF2 kinase on drug sensitivity depends on functional p53. Additionally, the effect of DOX treatment on the induction of p53 and cyclin-dependent kinase inhibitor p21 (WAF1), whose expression is known to be regulated by p53, is determined. The expression of p53 is undetectable in both untreated eEF2 kinase$^{-/-}$ and untreated wild type MEFs. After treatment with 600 ng/ml of DOX for 24 h, p53 is similarly induced in both eEF2 kinase$^{-/-}$ and eEF2 kinase$^{+/+}$ MEFs. However, p21 WAF1 is induced significantly more strongly in eEF2 kinase$^{+/+}$ MEFs (FIGS. 3c and 3d). Expression of several p53 dependent genes in eEF2 kinase knockout and wild type cells is also determined after treatment with doxorubicin using RT-PCR. In addition to p21 WAF1, the induction of apoptosis-related genes, GADD45 and PIG3 is significantly higher in eEF2 kinase$^{+/+}$ DOX treated cells than in eEF2 kinase$^{-/-}$ DOX treated cells. These results suggest that although induction of p53 in eEF2 kinase knockout cells is comparable to that of the wild type, its transactivation activity is altered.

Long-term survival assays in eEF2 kinase$^{+/-}$, eEF2 kinase$^{+/+}$ and eEF2 kinase$^{-/-}$ mice reveal that knockout of eEF2 kinase results in a significant increase in maximal life span (FIG. 5a, b). Maximal lifespan, defined as the average age of the last 10% of surviving mice, is increased by approximately 30% in eEF2 kinase$^{-/-}$ mice (36.6 month) and approximately 18% in eEF2 kinase$^{+/-}$ mice (33.1 month) in comparison with eEF2 kinase$^{+/+}$ mice (28 month). Since increase in maximal life span is observed in both eEF2 kinase$^{-/-}$ and eEF2 kinase$^{+/-}$ mice, the complete elimination of eEF2 kinase is not required for the life span extending effect. The significant increase in maximal life span in eEF2 kinase knockout mice is not accompanied by an increase in median life span. Maximal life span is considered to be a key parameter in the measurement of longevity and its extension indicates a genuine slowing of the aging process. In contrast to maximal life span, which depends on the cumulative effect of many different factors related to aging, median life span is often determined by a single factor, that causes death in the majority of animals in the population and which may or may not be related to aging. Therefore the increase in maximal, but not median life span in eEF2 kinase$^{-/-}$ and eEF2 kinase$^{+/-}$ mice suggests that the decrease of eEF2 kinase affects aging per se.

The increased maximal life span in eEF2 kinase knockout mice can be related to increased cellular stress resistance. In addition there is a correlation between life span of various mammalian species and stress resistance of fibroblasts derived from them.

Increased maximal life span in eEF2 kinase knockout mice can also be related to altered regulation of p53 and p21. Increased activation of p53 is known to cause premature aging in mice and overexpression of p21 results in the induction of various genes associated with senescence and aging, including p66$^{SHC}$. Therefore, the reduced activation of p53 observed in eEF2 kinase$^{-/-}$ cells and the reduced induction of p21 that it leads to, can contribute to increased longevity in eEF2 kinase knockout mice.

Example 9

Sensitivity to Radiation

Gamma irradiation of mice: 8 to 12 week old mice are irradiated at a dose of 8 grays (Gy) of whole-body gamma irradiation produced by Caesium-137 source (Nordiom gammacell 40). Each cohort of mice consists of 10 mice including 5 males and 5 females.

Preparation of MEFs: Mouse embryonic fibroblasts (MEFs) are prepared from E13.5 embryos and immortalized by large T antigen via retrovirus infection. Virus is collected from the medium of transient triple-transfected 239T cells by three plasmids including VSV, gal/pol, and pBebe-neo TcDNA.

TUNEL assay: Cells are treated with or without 1.6 µM of doxorubicin for 24 hours. After treatment, cells are collected and fixed in 1% paraformaldehyde for 15 minutes on ice. Cells are stored in 75% ethanol at −20° C. until staining, which is performed according to the manufacturer's instructions (In Situ Cell Death Detection kit, Roche). Apoptotic cells are labeled with fluorescein and counted by flow cytometry.

The effect of eEF2 kinase deficiency on the short-term survival of mice under stress is analyzed. Mice are irradiated with 8 Gy of whole-body γ-irradiation. After irradiation, 50% of wild type mice die within 16 days; however none of the eEF2K-deficient mice die during the same interval (FIG. 6a).

Within one month after irradiation the hair color of surviving, normally black wild type mice turns grey but, unexpectedly, this does not occur in eEF2 kinase deficient mice (FIG. 6b). In addition, significant hair loss is noted in irradiated wild type mice, but not in irradiated eEF2K−/− mice.

Because γ-irradiation is known to induce apoptosis, the increased resistance to γ-irradiation observed in eEF2K-deficient mice may be due to a corresponding increase in the resistance of eEF2K-deficient cells to apoptosis. To test this possibility, the effect of eEF2K deficiency on apoptosis in cells isolated from eEF2K−/− mice is analyzed. Cells from eEF2K deficient mice are significantly more resistant to apoptosis induced by doxorubicin or hydrogen peroxide. As can be seen in FIG. 7a, significant cell death is observed in wild type mouse embryonic fibroblasts (MEFs) treated for 24 hours with 1.6 µM doxorubicin. However, much less cell death is observed in eEF2K-deficient cells treated in the same manner. The results of the TUNEL assay suggest that the reduction in cell death in eEF2K-deficient cells is due to decreased apoptosis (FIG. 7b). To verify that the decreased apoptosis is due to the absence of eEF2K, eEF2K cDNA is introduced into eEF2K-deficient MEFs. As can be seen in FIG. 7c, after treatment with hydrogen peroxide or doxorubicin, MEFs carrying eEF2K cDNA have more activated caspase 3 than eEF2K-deficient cells from which they are derived, thus confirming that eEF2K enhances apoptosis.

Example 10

Distribution of Phosphorylated eEF2

Western blot and immunohistochemistry: Antibodies against phosphorylated eEF2 and cleaved caspase 3 (5A1) are purchased from Cell SignalingTech. Antibody against mouse eEF2K is purchased from BD Biosciences. Antibody against actin (AC-40) is purchased from Sigma. Mouse liver tissue is obtained from eEF2K knock-out and aged-matched wild type adult mice and lysed in buffer with 50 mM Tris-HCl in pH 8.0, 2 mM EDTA, 75 mM NaCl, 0.05 mM DTT, 1 mM PMSF, 0.5% Triton X-100, 10% glycerol, and 1 tablet of protease inhibitor cocktail (CPI, Roche)/10 ml. After $H_2O_2$ or doxorubicin treatment, cells are lysed in SDS containing buffer (20 mM HEPES in pH 7.5, 50 mM NaCl, 25 mM KCl, 10 mM DTT, 3 mM benzamidine, 1% SDS, 1 mM sodium orthovanadate, sodium pyrophosphate, 1 tablet of CPI/10 ml). Western blotting and immunohistochemistry are performed according to the manufacturer's instructions (Cell SignalingTech).

Using antibody that specifically recognizes phosphorylated eEF2, the distribution of phosphorylated eEF2 in tissue culture cells and in various human tissues is analyzed. Western blot analysis reveals strong and persistent phosphorylation of eEF2 in NIH3T3 cells treated with hydrogen peroxide for various time periods (FIG. 8a). Immunocytochemical analysis of these cells show that levels of phosphorylated eEF2 are high in rounding cells and highest in cells undergoing apoptosis, whereas no significant phosphorylation of eEF2 is detected in control cells grown under standard conditions (FIG. 8b). Similarly, treatment of HeLa cells with hydrogen peroxide results in a dramatic and selective increase in phosphorylation of eEF2 in apoptotic cells with condensed chromatin (FIG. 8c).

Various human tissues are also examined for the presence of phosphorylated eEF2 using human multiple tissue arrays. Phosphorylated eEF2 is not detectable in most tissues. However, significant phosphorylation of eEF2 in lymph nodes is observed (FIGS. 8d-e). Particularly intense phosphorylation is found in macrophages that likely represent staining of phagocytized lymphocytes undergoing apoptosis (FIG. 8e). Phosphorylated eEF2 is also detected in pyramidal neurons in histological sections of Alzheimer's disease brains (FIG. 8f), but not in neurons of neurologically normal, age-matched control brains (FIG. 8g). These results suggest that activation of eEF2 kinase is associated with the cellular response to stress and cell death.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and script of the invention, and all such variations are intended to be included within the scope of the following claims.

---

We claim:

1. A method of reducing damage to a cell caused by cytotoxic agents or increasing resistance to damage to a cell caused by cytotoxic agents, comprising delivering to tissues exposed to a cytotoxic agent an amount of a compound that decreases phosphorylation of eEF2 kinase substrate by eEF2 kinase, wherein said amount is effective to reduce said cell damage.

2. The method of claim 1, wherein said phosphorylation of said eEF2 kinase substrate is decreased by decreasing eEF2 kinase catalytic activity in said cell.

3. The method of claim 1, wherein said phosphorylation of eEF2 kinase substrate is decreased by reducing expression of a gene encoding the eEF2 kinase in said cell.

4. The method of claim 3, wherein said expression of a gene encoding the eEF2 kinase is reduced by contacting said gene, or an mRNA transcribed from said gene, with a compound comprising a polynucleotide selected from the group consisting of an antisense oligonucleotide, a ribozyme, an siRNA, and an shRNA.

5. The method of claim 4, wherein said compound comprises a polynucleotide comprising a nucleotide sequence complementary to a nucleotide sequence encoding a polypeptide comprising the amino acid sequence of SEQ ID NO: 2.

6. The method of claim 5, wherein said compound comprises a nucleotide sequence complementary to a nucleotide sequence comprising the nucleotide sequence of SEQ ID NO: 1.

7. The method of claim 1, wherein said cell damage is caused by treatment increased acidity, oxidative stress, exposure of said cell to camptothecin (CPT), exposure of said cell to doxorubicin (DOX), and exposure of said cell to taxol.

* * * * *